(12) United States Patent
Aoki

(10) Patent No.: US 6,382,015 B1
(45) Date of Patent: May 7, 2002

(54) AIR-FUEL RATIO SENSOR RESISTANCE DETECTING APPARATUS

(75) Inventor: Keiichiro Aoki, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/290,039

(22) Filed: Apr. 12, 1999

(30) Foreign Application Priority Data

Jun. 11, 1998 (JP) ............................................. 10-163764

(51) Int. Cl.[7] ...................... G01N 33/497; G01M 19/00
(52) U.S. Cl. ...................................... 73/23.32; 73/118.1
(58) Field of Search ............................. 73/118.1, 23.32; 204/424

(56) References Cited

U.S. PATENT DOCUMENTS

| | | | | |
|---|---|---|---|---|
| 5,547,552 A | * | 8/1996 | Hasegawa et al. | 204/406 |
| 6,065,327 A | * | 5/2000 | Fukaya et al. | 73/23.32 |
| 6,092,368 A | * | 7/2000 | Ishii et al. | 73/118.1 |
| 6,136,170 A | * | 10/2000 | Inoue et al. | 204/424 |

FOREIGN PATENT DOCUMENTS

| | | | | |
|---|---|---|---|---|
| JP | 9-29364 | 11/1997 | | |
| JP | 2000028575 A | * | 1/2000 | G01N/27/41 |

\* cited by examiner

*Primary Examiner*—Benjamin R. Fuller
*Assistant Examiner*—Maurice Stevens
(74) *Attorney, Agent, or Firm*—Kenyon & Kenyon

(57) ABSTRACT

An apparatus for detecting a resistance of an air-fuel ratio sensor has an air-fuel ratio sensor element, a heater for activating the sensor element, an air-fuel ratio detecting device for detecting an air-fuel ratio in a detection object gas detected by the sensor element, a gas condition detecting device for detecting a gas detection of the detection-object gas, a device for detecting an impedance of the sensor element and a device for correcting the impedance of the sensor element in accordance with the gas condition. A cumulative amount of electric power supplied to the heater during a predetermined period of time is calculated. Based on the calculated cumulative amount of electric power, the impedance of the sensor element is corrected. In accordance with the cumulative amount of electric power supplied to the heater, it is determined whether the sensor element has a failure and an element temperature control target learned value is determined. A target impedance is calculated by correcting the learned value in accordance with the gas condition. Based on the calculated target value, the heater is controlled to prevent overheating of the sensor element and the heater.

7 Claims, 21 Drawing Sheets

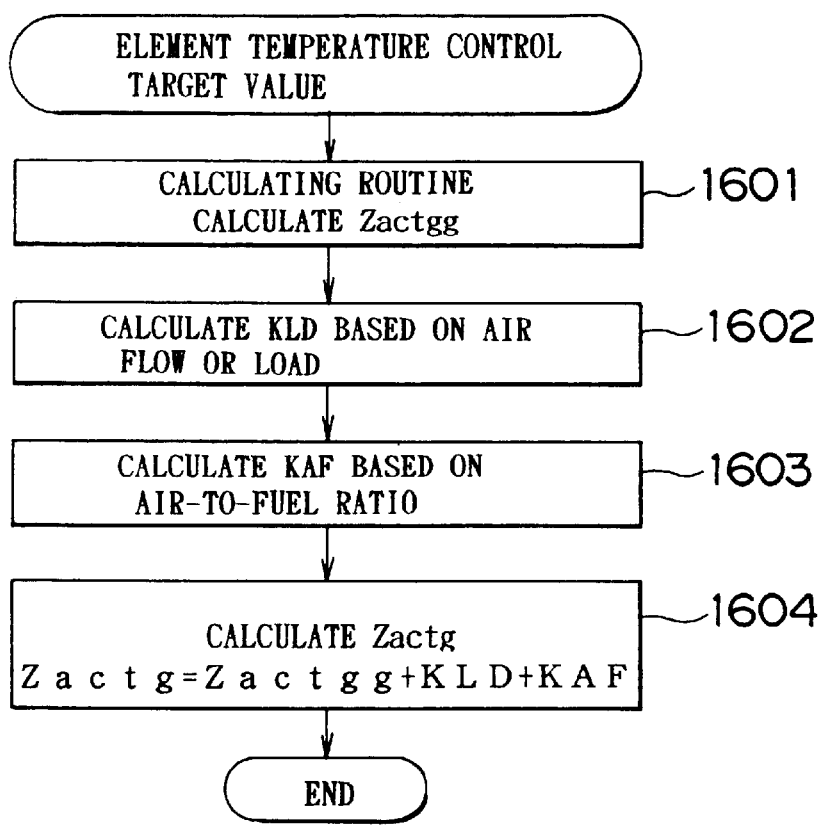

FIG. 18

| NE(rpm)<br>PM(mmHg) | 800 | 1600 | 2400 | 3000 | 3600 | 4200 |
|---|---|---|---|---|---|---|
| 150 | -8 | -5 | 0 | 0 | 5 | 10 |
| 300 | -5 | 0 | 0 | 5 | 10 | 10 |
| 50 | 0 | 0 | 5 | 5 | 10 | 15 |
| 600 | 0 | 5 | 5 | 10 | 10 | 15 |
| 750 | 5 | 5 | 10 | 10 | 15 | 15 |

FIG. 19

| A/F | 12 | 14.5 | 18 | 25 | 40 | 80 |
|---|---|---|---|---|---|---|
| KAF | 5 | 0 | -5 | -8 | -12 | -16 |

ELEMENT TEMPERATURE CONTROL TARGET LEARNED VALUE CALCULATING ROUTINE

2501 — CALCULATE HTWAV FROM $\Sigma HTW_i$
$HTWAV = \Sigma HTW_i$ / NUMBER OF SUMMINGS

2502 — CALCULATE ZACOT FROM HTWAT, USING MAP.

2503 — CALCULATE $Zactgg_i$
$Zactgg_i = Zactgg_{i-1} + ZACOT$

2504 — STORE LEARNED VALUE INTO BACKUP RAM (SRAM)
$Zactggb$ (STORED VALUE) = $Zactgg_i$

END

| HTWAV (watt·h) | 18 | 20 | 22 | 24 | 26 |
|---|---|---|---|---|---|
| ZACOT (Ω) | 0 | 0.5 | 1.0 | 1.5 | 2.0 |

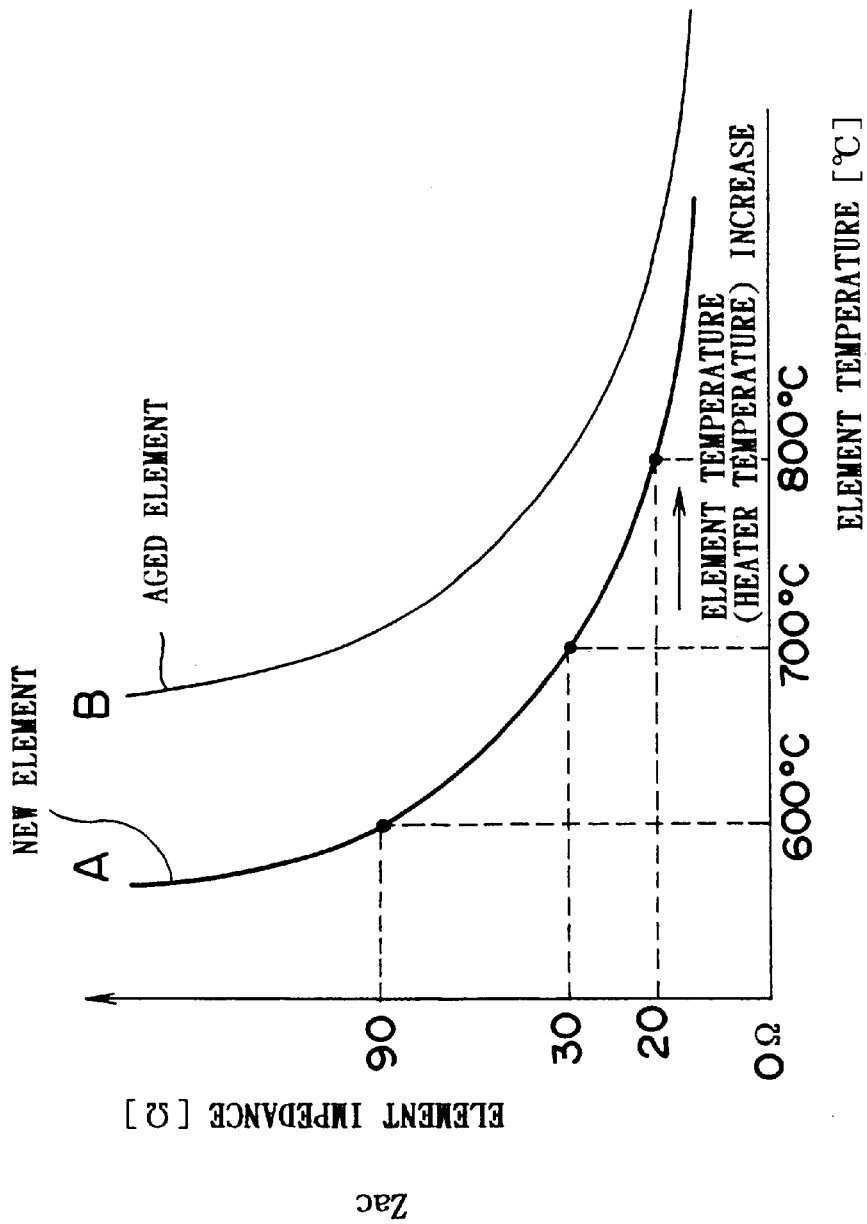

AIR-FUEL RATIO SENSOR RESISTANCE DETECTING APPARATUS

The disclosure of Japanese Patent Application Laid-open No. HEI 10-163764 filed on Jun. 11, 1998 including the specification, drawings and abstract is incorporated herein by reference in its entirety.

BACKGROUND OF THE INVENTION

1. Field of the Invention

The present invention relates to an apparatus for detecting the resistance of an air-fuel ratio sensor and, more particularly, to an air-fuel ratio sensor resistance detecting apparatus for detecting the impedance of an air-fuel ratio sensor used to detect an exhaust gas air-fuel ratio, for example, an oxygen concentration detector element.

2. Description of the Related Art

In order to allow a catalyst disposed in the exhaust system of an engine to remove a maximum amount of harmful components (for example, hydrocarbon (HC), carbon monoxide (CO), oxides of nitrogen (NOx) and the like)as from exhaust emissions, recent air-fuel ratio control technologies employ an air-fuel ratio sensor disposed in the exhaust system, and perform feedback control such that the exhaust air-fuel ratio detected by the air-fuel ratio sensor becomes a target air-fuel ratio, for example, the theoretical air-fuel ratio. An air-fuel ratio sensor normally employed by these technologies is a limiting current-type oxygen concentration detector element that outputs a limiting current proportional to a concentration of oxygen in exhaust gas from the engine. The limiting current-type oxygen concentration detector element makes it possible to linearly detect the exhaust air-fuel ratio based on the detected oxygen concentration over a wide range. Thus, the limiting current-type oxygen concentration detector element is useful for improving the air-fuel ratio control precision, or for performing lean-burn control.

The oxygen concentration detector element requires that the element be kept in an active state, in order to maintain high precision air-fuel ratio detection. Typically, when the engine is started, the element is immediately heated by electrifying a heater attached to the element, in order to quickly activate the element. The electrification of the heater is then controlled so as to maintain the active state of the element.

FIG. 27 is a graph indicating the correlation between the temperature and the impedance of oxygen concentration detector elements. The temperature and the impedance of an oxygen concentration detector element (hereinafter, simply referred to as an "element") normally have a correlation indicated by line A in FIG. 27, that is, a relationship in which the element impedance diminishes with an increase in the element temperature. Based on this relationship, the aforementioned heater electrification control detects the element impedance, and derives therefrom an element temperature, and performs a feedback control such that the derived element temperature becomes a desired activation temperature, for example, 700° C. For example, if the element impedance Zac is equal to or greater than 30Ω (Zac≧30), i.e., the element impedance corresponding to the initial control element temperature 700° C., that is, if the element temperature is equal to or lower than 700° C., as indicated by line A in FIG. 27, the heater is electrified. If Zac is less than 30Ω (Zac<30), that is, if the element temperature is higher than 700° C., the electrification of the heater is discontinued. Through this control, the element temperature is kept equal to or higher than 700° C., i.e., the activation temperature of the element, so that the active state of the element is maintained. During electrification of the heater, an amount of power supply needed to eliminate the deviation of the element impedance from the target value (i.e., Zac−30) is determined, and duty control is performed so as to supply that amount of power to the heater.

A method for detecting the temperature of an oxygen concentration sensor, disclosed in, for example, Japanese Patent Application Laid-open No. HEI 9292364, detects the impedance of the oxygen concentration detector element by applying a DC voltage for air-fuel ratio detection together with a superimposed AC voltage having a frequency suitable for detecting the element temperature, for example, 5 kHz, to the element, and measuring the current through the element after the AC voltage superimposition. Based on the superimposed applied voltage and the measured current, an element impedance is detected.

However, the element impedance detected by the aforementioned method for detecting the resistance of an oxygen concentration sensor element has the following problems. An oxygen concentration sensor disposed in an exhaust passage of an internal combustion engine undergoes aging deterioration of electrode portions of the element due to exhaust gas heat or deposit on interiors or surfaces of the electrodes of the element, so that the correlation between the element impedance and the element temperature changes as indicated by line B in FIG. 27. That is, as the sensor element deteriorates, the detected element impedance values deviate. Furthermore, oxygen concentration sensors disposed in exhaust passages also experience deviations in detected impedance values due to the changing exhaust gas conditions of depending on the intake air flow, the load condition of the engine, the exhaust air-fuel ratio, and the like.

Deviations of the detected impedance values as described above naturally cause undesired events. For example, even if the target impedance is 30Ω and the present true element impedance is 30Ω, the element impedance may be falsely detected as 20Ω due to a deviation as mentioned above, so that the element temperature is determined to be 800° C. In that case, the heater is controlled so as to reduce the element temperature. If such control is continued, the sensor element is cooled below the activation temperature of 700° C., thus failing to maintain the active state. As a result, the air-fuel ratio control precision deteriorates, and exhaust emission becomes degraded.

Furthermore, if the target impedance is 30Ω and the present true element impedance is 30Ω, the element impedance may be falsely detected as 90Ω due to a deviation as mentioned above, so that the element temperature is determined to be 600° C. In that case, the heater is controlled to increase the element temperature. If such control is continued, the sensor element temperature exceeds the activation temperature of 700° C., that is, the sensor element is overheated. As a result, deterioration of the sensor element is accelerated, and the service life thereof is shortened.

SUMMARY OF THE INVENTION

Accordingly, it is an object of the present invention to provide an air-fuel ratio sensor resistance detecting apparatus that prevents deterioration of the sensor element due to overheating thereof and prevents deterioration of a heater resistor due to excessive power supply thereto even when the sensor element deteriorates over time or when the condition of a detection object gas changes.

It is another object of the invention to provide an air-fuel ratio sensor resistance detecting apparatus that determines whether the air-fuel ratio sensor element has failed.

To achieve the aforementioned and other objects, one aspect of the invention provides an air-fuel ratio sensor resistance detecting apparatus including an oxygen concentration detecting element that detects an oxygen concentration in a detection object gas (e.g., exhaust gas from an engine), a heater for activating the oxygen concentration detecting element, an air-fuel ratio detection device for detecting an electric current through the oxygen concentration detecting element proportional to the oxygen concentration in the detection object gas by applying a voltage to the oxygen concentration detecting element, the air-fuel ratio detection device detecting an air-fuel ratio of the detection object gas based on the electric current. The air-fuel ratio sensor resistance detecting apparatus further includes a gas condition detection device for detecting a condition of the detection object gas, an impedance detection device for detecting an impedance of the oxygen concentration detecting element by applying a voltage to the oxygen concentration detecting element, and a correction device for correcting the impedance detected by the impedance detection device, in accordance with the gas condition.

This apparatus corrects the impedance of the oxygen concentration detecting element in accordance with the gas condition of the detection object gas detected by the oxygen concentration detecting element, and corrects the target impedance for the oxygen concentration detecting element. Therefore, the apparatus is able to properly control the target impedance in accordance with the gas condition and prevent overheating of the oxygen concentration detecting element and the heater.

In accordance with another aspect of the invention, an air-fuel ratio sensor resistance detecting apparatus includes an oxygen concentration detecting element that detects an oxygen concentration in a detection object gas, a heater for activating the oxygen concentration detecting element, an air-fuel ratio detection device for detecting an electric current flowing through the oxygen concentration detecting element, the current being proportional to an oxygen concentration in the detection object gas, upon application of a voltage to the oxygen concentration detecting element, an electric power calculation device for calculating an amount of electric power supplied to the heater, an impedance detection device for detecting an impedance of the oxygen concentration detecting element by applying a voltage to the oxygen concentration detecting element, and a correction device for correcting the impedance detected by the impedance detection device, in accordance with the amount of electric power supplied to the heater.

This apparatus uses the amount of electric power calculated by the electric power calculation device as a parameter corresponding to the deterioration of the sensor element (e.g., resulting from aging changes) to correct the impedance of the oxygen concentration detecting element and therefore correct a target impedance set for the oxygen concentration detecting element, in accordance with the amount of electric power. Therefore, the apparatus is able to properly control the target impedance in accordance with the deterioration of the sensor element despite aging changes and prevent overheating of the oxygen concentration detecting element and the heater.

The impedance detection device may detect the impedance of the oxygen concentration detecting element by applying a voltage obtained by superimposing an AC voltage on a DC voltage to the oxygen concentration detecting element. In that case, the impedance of the oxygen concentration detecting element can be detected within a short time.

BRIEF DESCRIPTION OF THE DRAWINGS

The foregoing and further objects, features and advantages of the present invention will become apparent from the following description of a preferred embodiment with reference to the accompanying drawings, wherein like numerals are used to represent like elements and wherein:

FIG. 16 is a flowchart illustrating a target impedance calculating routine;

FIG. 17 illustrates a map for deriving an impedance correction amount from the intake air flow;

FIG. 18 illustrates a map for deriving an impedance correction amount from the engine load condition;

FIG. 19 illustrates a map for deriving an impedance correction amount from the air-fuel ratio of the engine;

FIG. 27 is a graph indicating a correlation between the temperature and the impedance of an oxygen concentration detector element.

DETAILED DESCRIPTION OF PREFERRED EMBODIMENT

A preferred embodiment of the present invention will be described in detail hereinafter with reference to the accompanying drawings.

Figure 1:
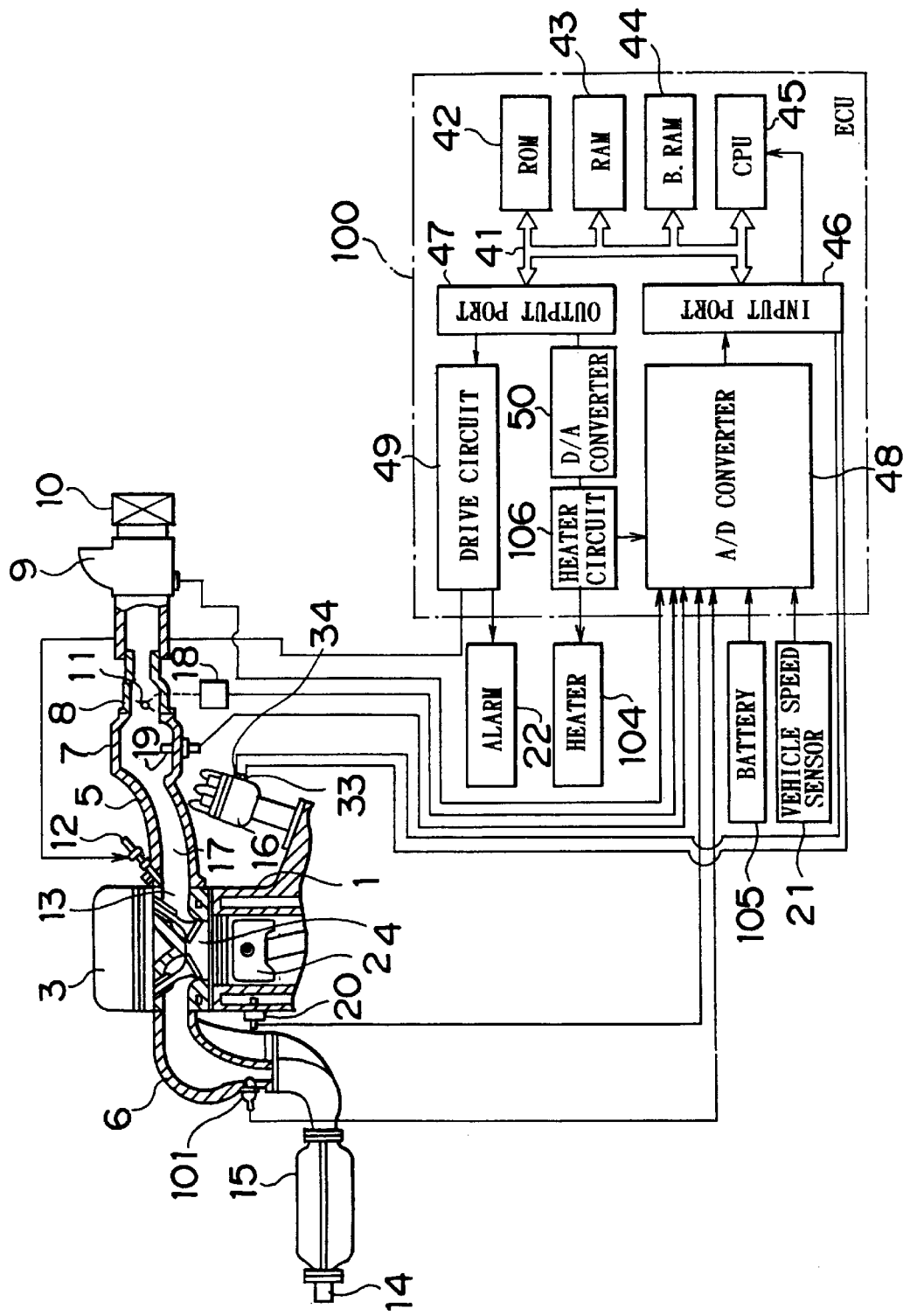
FIG. 1 is a schematic illustration of the construction of a preferred embodiment of the air-fuel ratio sensor resistance detecting apparatus of the invention.

FIG. 1 is a schematic illustration of the construction of the preferred embodiment of the air-fuel ratio sensor resistance detecting apparatus of the invention.

Referring to FIG. 1, an engine 1 has a piston 2, a cylinder head 3, a combustion chamber 4, an intake manifold 5 and an exhaust manifold 6. The intake manifold 5 is connected to an air cleaner 10 via a surge tank 7, an intake duct 8 and an air flow meter 9. A throttle valve 11 is disposed in the intake duct 8. A fuel injection valve 12 is mounted to the intake manifold 5 and directed toward an intake port 13. The exhaust manifold 6 is connected to an exhaust pipe 14. Disposed in the exhaust pipe 14 is a catalyst converter 15 containing a three-way catalytic device capable of simultaneously reducing the amounts of three components of the exhaust, that is, HC, CO and $NO_x$ and also capable of storing oxygen therein.

An electronic control unit (ECU) 100 is formed by a digital computer having a ROM 42, a RAM 43, a backup RAM 44, a CPU 45, an input port 46 and an output port 47 that are interconnected by a bi-directional bus 41. The air flow meter 9 generates an output voltage proportional to the flow of intake air. The output voltage signal is inputted to the input port 46 via an A/D converter 48. An air-fuel ratio sensor 101 is disposed in an upstream portion of the exhaust manifold 6. The air-fuel ratio sensor 101 detects the oxygen concentration in the exhaust gas. A signal outputted by the air-fuel ratio sensor 101 is inputted to the input port 46 via the A/D converter 48.

The opening of the throttle valve 11 disposed in the intake duct 8 is varied in accordance with the operation of an accelerator pedal (not shown). The throttle valve 11 is provided with a throttle position sensor 18 that has an idle switch for detecting a completely closed state of the throttle opening. The throttle position sensor 18 is connected to the ECU 100. An on-off signal XIDLE from the idle switch of the throttle position sensor 18 is inputted to the input port 46 of the ECU 100. An analog voltage signal proportional to the throttle opening is inputted to the input port 46 via the A/D converter 48.

The surge tank 7 is provided with a pressure sensor 19 for detecting the absolute pressure in an exhaust passage. The pressure sensor 19 outputs an analog voltage signal proportional to the intake air pressure, to the input port 46 via the A/D converter 48.

The cylinder head 3 is provided with a water temperature sensor 20 for detecting the engine cooling water temperature in a water jacket. The water temperature sensor 20 outputs an analog voltage signal proportional to the cooling water temperature of the engine 1, to the input port 46 via the A/D converter 48.

A battery 105 is connected to the ECU 100. The voltage from the battery 105 is inputted to the input port 46 via the A/D converter 48 in the ECU 100. A vehicle speed sensor 21 for detecting the speed of a vehicle in which the engine 1 is installed is also connected to the ECU 100. An analog voltage output of the vehicle speed sensor 21 is inputted to the input port 46 via the A/D converter 48 in the ECU 100.

A distributor 16 is provided with two crank angle sensors 33, 34. The crank angle sensor 33 detects a reference position every 720° CA in terms of crank angle, and correspondingly generates an output pulse signal. The crank angle sensor 34 detects a position every 30° CA in terms of crank angle, and correspondingly generates an output pulse signal. The output pulse signals from the crank angle sensors 33, 34 are inputted to the input port 46. The output pulse signals from the crank angle sensor 34 are also inputted to an interrupt terminal of the CPU 45. Based on the output pulse signals from the crank angle sensors 33, 34, the CPU 45 calculates, for example, a revolution speed of the engine 1.

The output port 47 of the ECU 100 is connected to the fuel injection valve 12 via a drive circuit 49. The amount of fuel injected from the fuel injection valve 12 into an intake passage 17 toward the intake port 13 is controlled by changing the open valve duration of the fuel injection valve 12 opened by the drive circuit 49 so that the air-fuel ratio becomes equal to a target air-fuel ratio, for example, the theoretical air-fuel ratio in this embodiment. The output port 47 is also connected to an alarm 22 via the drive circuit 49. The alarm 22 is energized when it is determined that an air-fuel ratio sensor element 102 or a heater 104 has deteriorated excessively.

An interrupt of the CPU 45 occurs when an A/D converting operation by the A/D converter 48 ends, or when an output pulse signal from the crank angle sensor 34 is received. Digital data inputted to the input port 46 via the A/D converter 48 is read immediately when the data is A/D converted. The read data is stored in the RAM 43. The revolution speed NE of the engine 1 is also calculated every time an output pulse signal from the crank angle sensor 34 is inputted to the interrupt terminal of the CPU 45. The calculated engine revolution speed NE is stored in the RAM 43. That is, the data stored in the RAM 43 regarding the engine 1 is constantly updated.

The heater 104 is provided to activate the sensor element of the air-fuel ratio sensor 101. In an operation described below, digital data calculated by the CPU 45 is outputted from the output port 47 to a D/A converter 50, whereby the data is converted into an analog voltage. Therefore, electric power is supplied to the heater 104 via a heater circuit 106.

Figure 2:
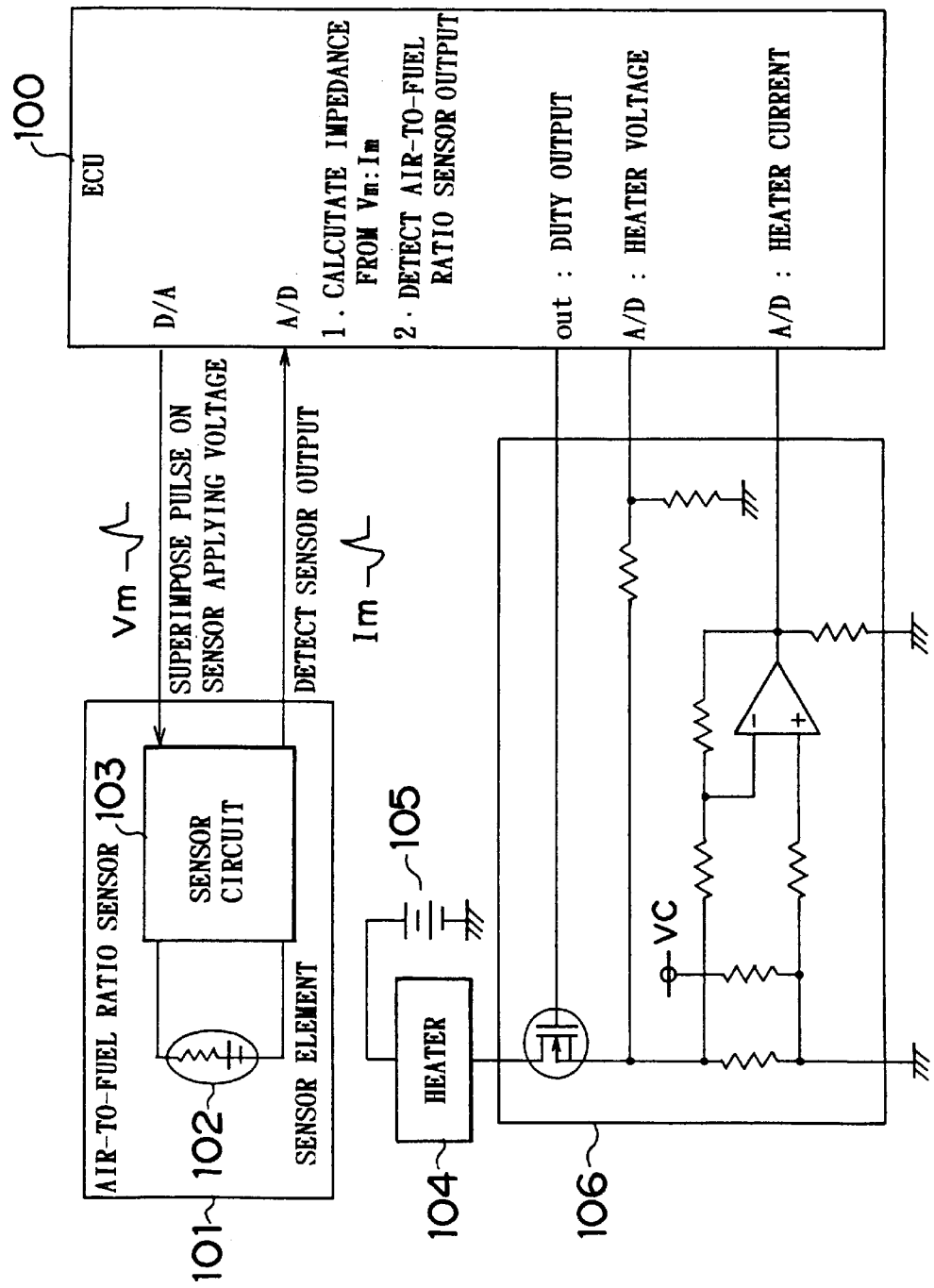
FIG. 2 is a diagram illustrating control of an air-fuel ratio sensor and a heater shown in FIG. 1.

FIG. 2 is a diagram illustrating the control of the air-fuel ratio sensor 101 and the heater 104 shown in FIG. 1. The air-fuel ratio sensor 101 for detecting the exhaust air-fuel ratio in the exhaust system of the engine 1 shown in FIG. 1 is substantially made up of an air-fuel ratio sensor element (hereinafter, simply referred to as a "sensor element") 102 and an air-fuel ratio sensor circuit (hereinafter, simply referred to as a "sensor circuit") 103. The sensor circuit 103 applies a voltage to the sensor element 102. The sensor circuit 103 receives an analog voltage from the ECU 100, and applies a voltage in accordance with the received voltage to the sensor element 102. The ECU 100 converts digital data calculated by an operation described below, into an analog voltage by using the D/A converter 50 provided in the ECU 100, and outputs the analog voltage to the sensor circuit 103. Along with the application of the voltage, the ECU 100 detects the current through the sensor element 102 that varies in proportion to the oxygen concentration in a detection object gas, i.e. exhaust gas. In order to detect the current, the ECU 100 receives an analog voltage corresponding to the current through the sensor element 102, from the sensor circuit 103 via the A/D converter 48. Then, the ECU 100 converts the analog voltage into digital data, and uses the digital data in the operation described below.

The output from the air-fuel ratio sensor 101 cannot be used for air-fuel ratio control unless the sensor element 102 is in an active state. Therefore, when the engine 1 is started, the ECU 100 supplies power from the battery 105 to the heater 104 to energize the heater 104 to quickly activate the sensor element 102. After the sensor element 102 is activated, the ECU 100 supplies power to the heater 104 to maintain the active state of the sensor element 102. The sensor circuit 103 has an integrating circuit therein, so that rectangular pulses inputted to the sensor circuit 103 from the ECU 100 are converted into sine wave-like pulse voltages, and the sine wave-like pulse voltages are applied to the sensor element 102. Therefore, errors in detecting the output current of the sensor element due to high-frequency noise can be prevented.

As the resistance of the sensor element 102 depends on the temperature of the sensor element 102, more specifically, the resistance of the sensor element 102 diminishes with an increase in the sensor element temperature, as indicated in FIG. 27, the ECU 100 performs a control such that the temperature of the sensor element 102 is kept at a target temperature, for example, 700° C., by supplying power to the heater 104 so that the resistance of the sensor element 102 becomes a resistance value corresponding to a temperature at which the active state of the sensor element 102 is maintained, for example, 30Ω. Furthermore, using the A/D converter 48 provided in the ECU 100, the ECU 100 receives from the heater circuit 106 the voltage across the heater 104 and an analog voltage corresponding to the current through the heater 104, and converts the voltages into digital data, and uses the digital data for operations described below. For example, the ECU 100 calculates a value of the resistance of the heater 104 and, based on the resistance value, supplies the heater 104 with an amount of power in accordance with the engine operating condition, and controls the temperature of the heater 104 to prevent over-heating of the heater 104.

Figure 3A:
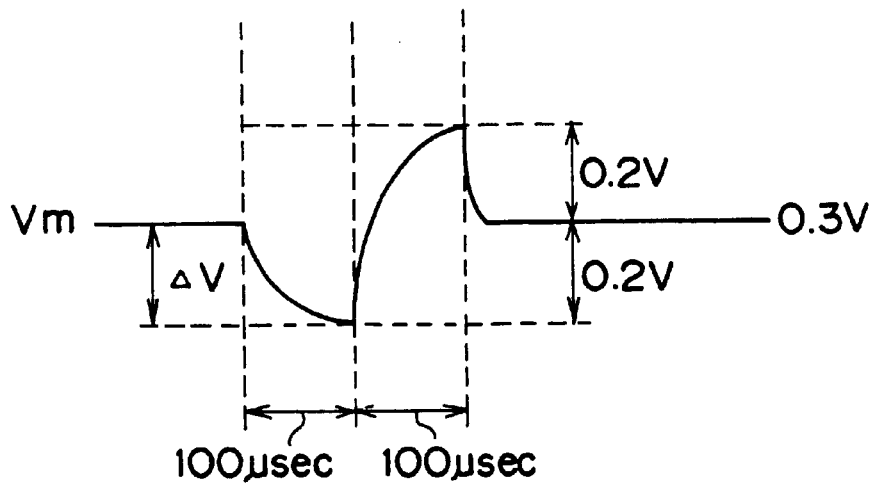
FIG. 3A shows the waveform of an input voltage applied to the sensor element.
Figure 3B:
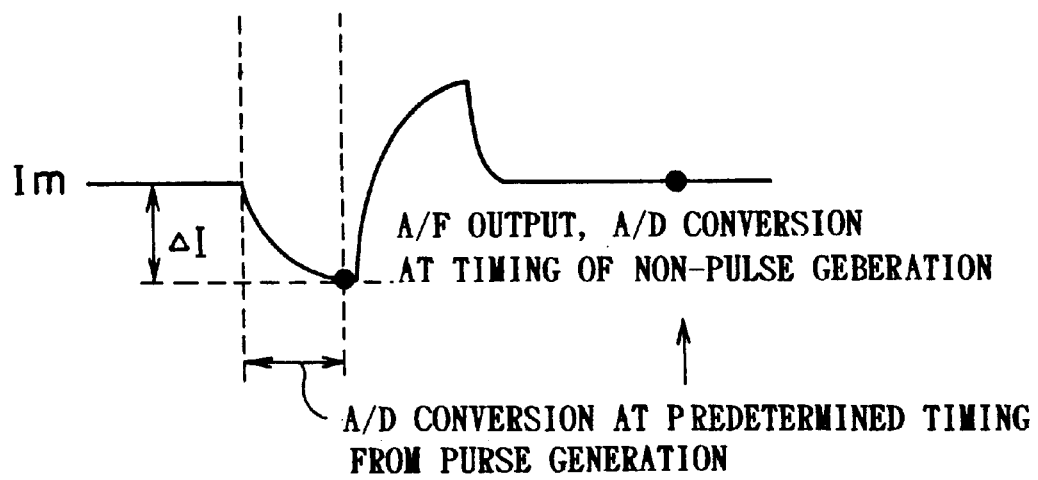
FIG. 3B shows the waveform of a detected output current from the air-fuel ratio sensor.

FIGS. 3A and 3B are diagrams indicating signals inputted to and outputted from the air-fuel ratio sensor 101. FIG. 3A shows the waveform of an input voltage applied to the sensor element 102. FIG. 3B shows the waveform of a detected output current from the air-fuel ratio sensor 101. In the diagrams in FIGS. 3A and 3B, the horizontal axis indicates time, and the vertical axis indicates voltage or current. As indicated in FIG. 3A, a DC voltage of 0.3 V is applied as an input voltage Vm to the air-fuel ratio sensor 101. In order to measure the impedance of the sensor element 102, the ECU 100 applies a pulse voltage of ±2 V having a first frequency (for example, 5 kHz) superimposed on the DC voltage 0.3 V, to the air-fuel ratio sensor 101, by executing a routine described below. As indicated in FIG. 3B, the detected output current Im from the air-fuel ratio sensor 101 exhibits a value in accordance with the present oxygen concentration of the detection object gas while only the DC voltage of 0.3 V is being applied to the air-fuel ratio sensor 101. However, the output current Im changes when the pulse voltage of ±±0.2 V is superimposed on the DC voltage of 0.3 V supplied to the air-fuel ratio sensor 101. The ECU 100 detects the change in the output current from the air-fuel ratio sensor 101, and calculates the impedance of the sensor element 102 based on the detected change.

The structure of the air-fuel ratio sensor element 102, an equivalent circuit thereof, and the impedance characteristics of the element will be described below.

Figure 4A:
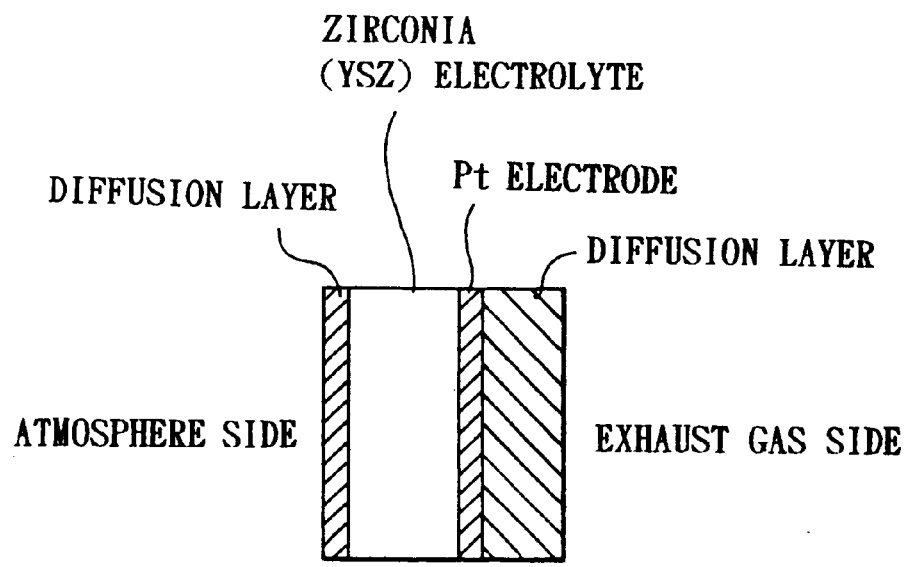
FIG. 4A is a sectional view an air-fuel ratio sensor element.
Figure 4B:
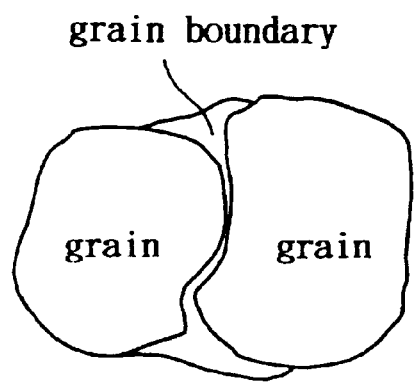
FIG. 4B is an enlarge fragmental view of an electrolyte portion of the air-fuel ratio sensor element.

FIGS. 4A and 4B illustrate the structure of the sensor element 102. FIG. 4A is a sectional view thereof. FIG. 4B is an enlarge fragmental view of an electrolyte portion of the sensor element 102.

Figure 5:
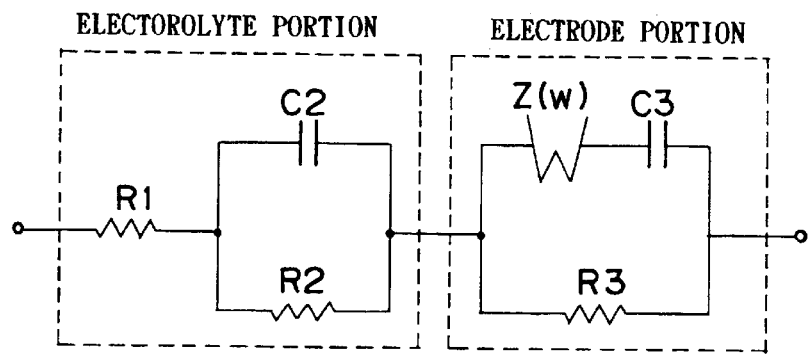
FIG. 5 is a diagram of the equivalent circuit of the air-fuel ratio sensor element.

FIG. 5 is a diagram of the equivalent circuit of the air-fuel ratio sensor element 102, where R1 represents the bulk resistance of the electrolyte made of, for example, zirconia (corresponding to a grain portion shown in FIG. 4B); R2 represents the grain boundary resistance of the electrolyte (corresponding to a grain boundary portion shown in FIG. 4B); R3 represents the interface resistance of an electrode formed from, for example, platinum; C2 represents the capacitance component in the grain boundary; C3 represents the capacitance component in the electrode interface; and Z(w) represents the impedance fraction (Warburg Impedance) caused by periodical changes in the interface concentration involved in the alternate current polarization.

Figure 6:
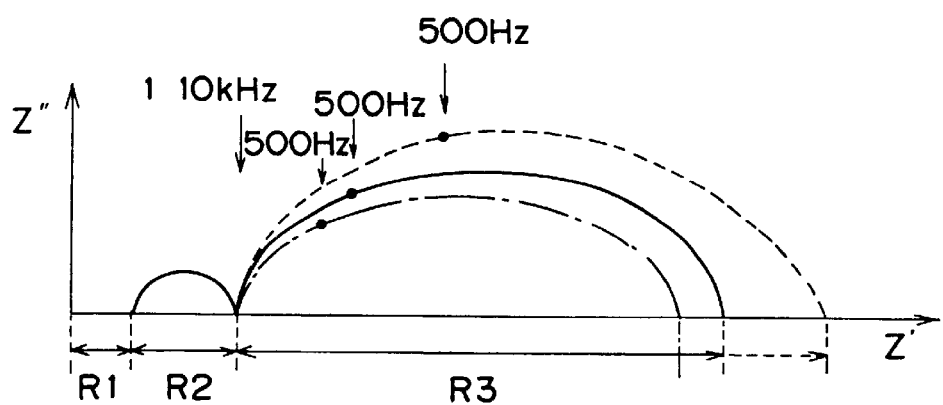
FIG. 6 is a diagram indicating the impedance characteristics of the air-fuel ratio sensor element.

FIG. 6 is a diagram indicating the impedance characteristics of the air-fuel ratio sensor element 102, where the horizontal axis indicates the real part Z' of the impedance Z, and the vertical axis indicates the imaginary part Z" thereof. The impedance Z of the sensor element 102 is expressed as Z'+jZ". The diagram of FIG. 6 indicates that the electrode interface resistance R3 converges to 0 as the frequency approaches 1–10 kHz. The dotted curve in the diagram indicates the element impedance occurring when a high oxygen concentration gas condition is detected by the sensor element 102. The dot-dash curve indicates the element impedance occurring when a low oxygen concentration gas condition is detected by the sensor element 102. From the impedance characteristics indicated by the dotted curve and the dot-dash curve, it can be seen that a great change occurs particularly in a portion R3.

Figure 7:
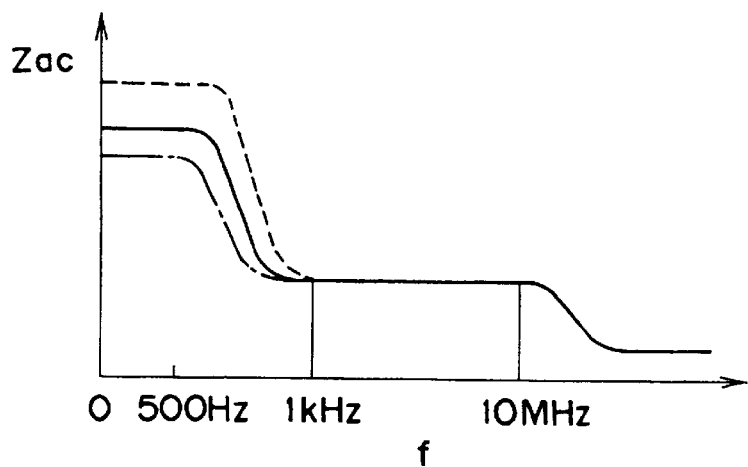
FIG. 7 is a diagram indicating a relationship between the impedance and the frequency of AC input voltage.

FIG. 7 is a diagram indicating a relationship between the impedance and the frequency of AC input voltage. The diagram of FIG. 7 is obtained through conversion of the diagram of FIG. 6, that is, conversion of the horizontal axis into frequency f and the vertical axis into impedance Zac. The diagram of FIG. 7 indicates that the impedance Zac converges to a predetermined value (R1+R2) in a frequency range of 1 kHz to 10 MHz, and that the impedance Zac decreases and converges to R1 at frequencies higher than 10 MHz. From this, it can be understood that frequencies in and around the range of 1 kHz to 10 MHz, where the impedance Zac remains substantially constant regardless of frequencies, are desirable to detect the impedance Zac in a stable state. In FIG. 7, the dotted curve and the dot-dash curve correspond to the impedance characteristics indicated in FIG. 6.

Figure 8:
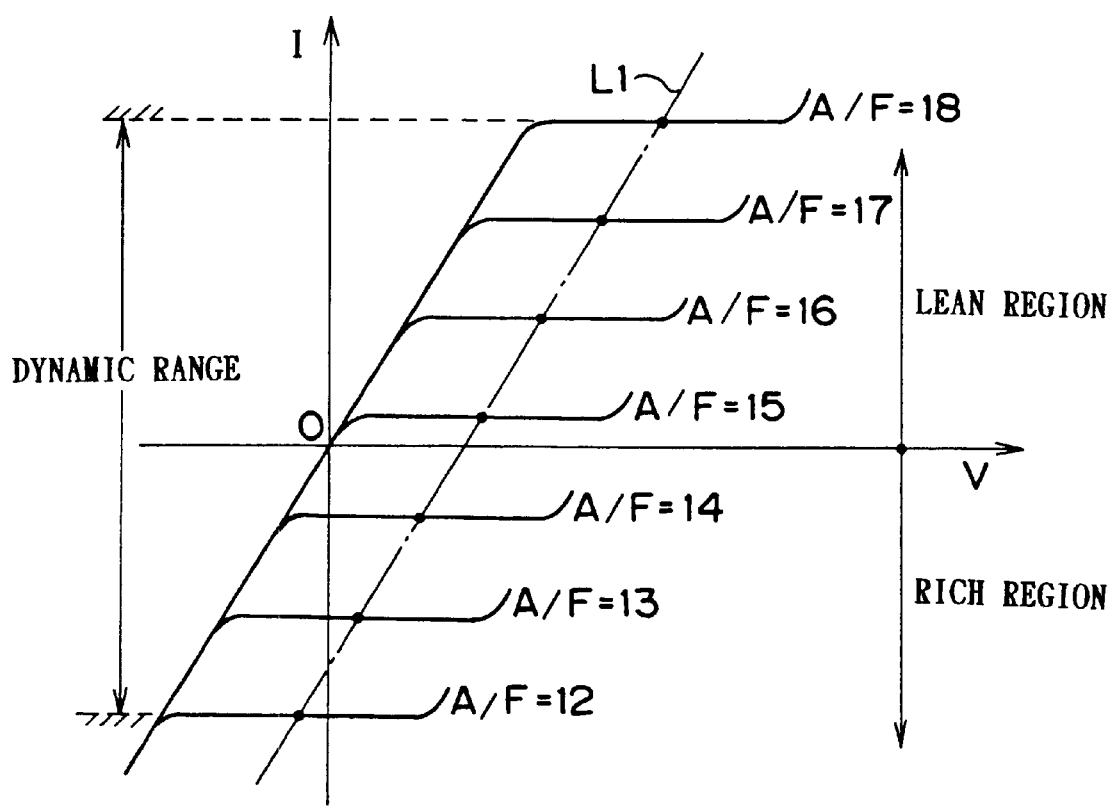
FIG. 8 is a diagram showing voltage-current characteristic curves of the air-fuel ratio sensor.

FIG. 8 is a diagram showing voltage-current characteristic curves of the air-fuel ratio sensor 101, where the horizontal axis indicates the voltage V applied to the sensor and the vertical axis indicates the output current I of the sensor. As indicated by the diagram of FIG. 8, the applied voltage V and the output current I have a substantially proportional relationship that the current value changes to a positive side as the air-fuel ratio changes to a lean side and the current value changes to a negative side as the air-fuel ratio changes to a rich side (see characteristic line L1 in FIG. 8). That is, the limiting current increases with changes in the air-fuel ratio to a leaner side, and decreases with changes in the air-fuel ratio to a richer side. When the output current I is 0 mA, the air-fuel ratio becomes the theoretical air-fuel ratio (about 14.5). The voltage-current characteristic depends on the element temperature, that is, the gradient of line L1 increases as the element temperature increases. In contrast, the limiting current value is not greatly affected by the element temperature, that is, the limiting current remains at a substantially constant value regardless of changes in the element temperature, if the air-fuel ratio remains constant.

A sensor element impedance calculating routine executed by the ECU 100 will be described in detail below.

Figure 9:
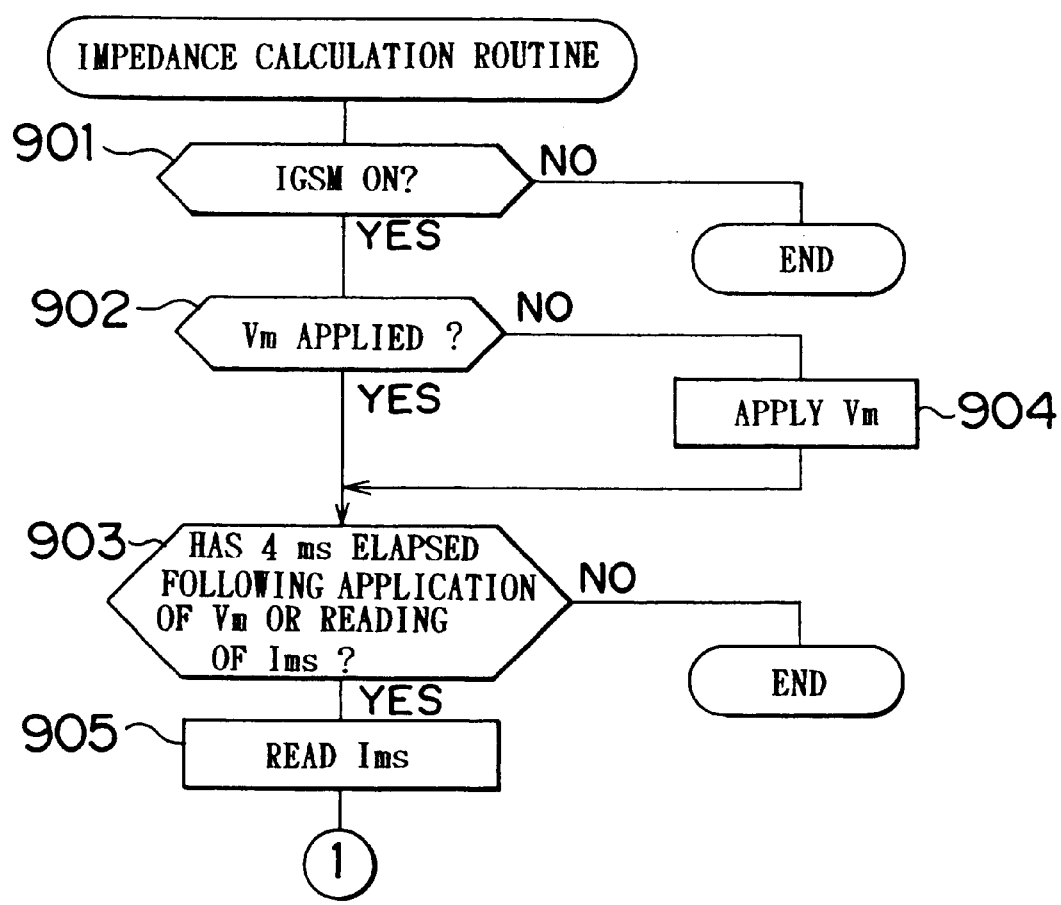
FIG. 9 is a flowchart illustrating an earlier portion of a sensor element impedance calculating routine.
Figure 10:
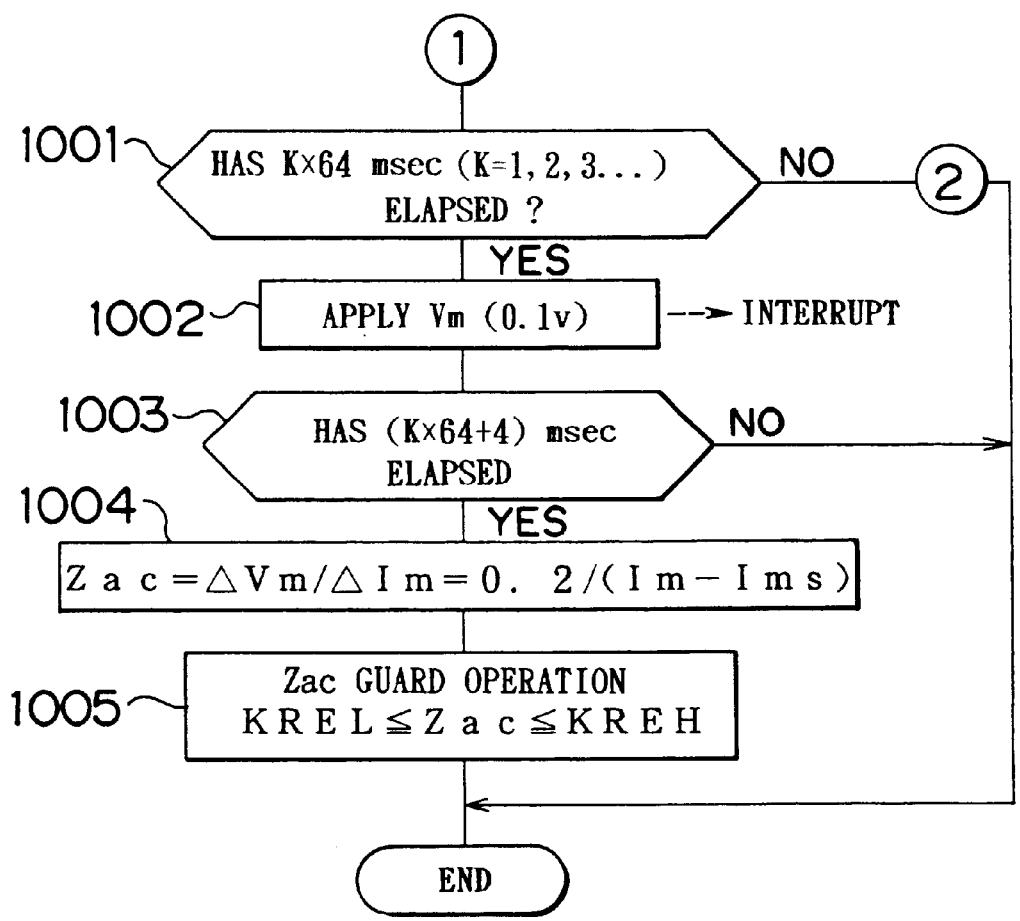
FIG. 10 is a flowchart illustrating a specific frequency superimposing operation in the sensor element impedance calculating routine.
Figure 11:
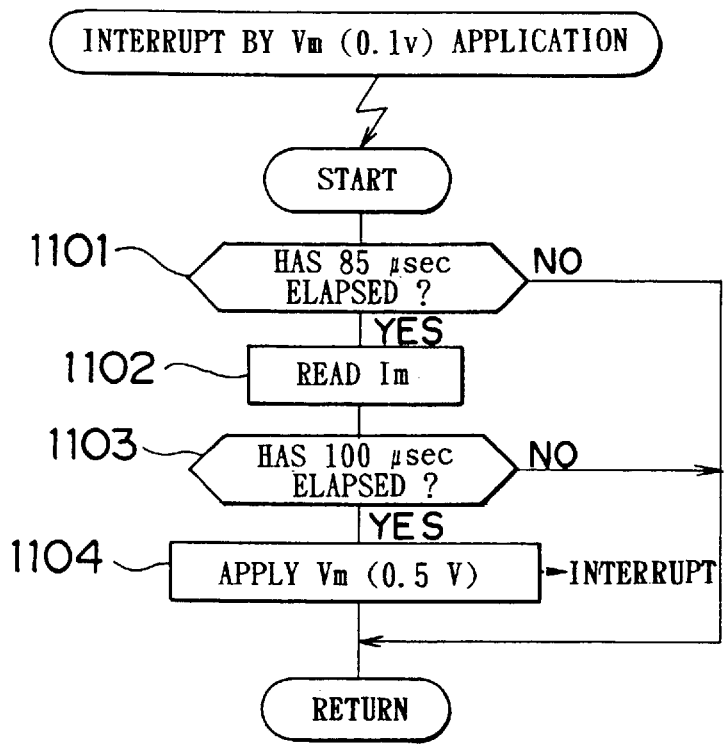
FIG. 11 is a flowchart illustrating a first interrupt routine needed in order to perform the specific frequency superimposing operation.
Figure 12:
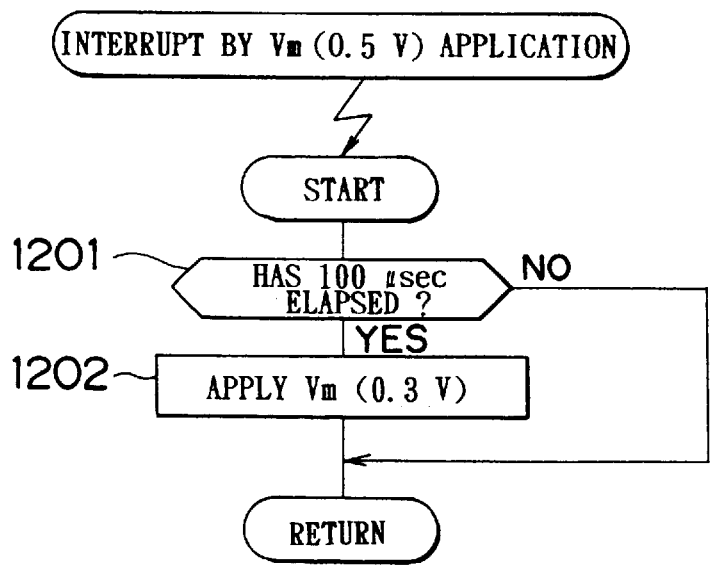
FIG. 12 is a flowchart illustrating a second interrupt routine needed in order to perform the specific frequency superimposing operation.

FIG. 9 is a flowchart illustrating an earlier portion of the sensor element impedance calculating routine. FIG. 10 is a flowchart illustrating the later portion of the routine. More specifically, the flowchart of FIG. 10 illustrates a specific frequency superimposing operation in the sensor element impedance calculating routine. FIGS. 11 and 12 are flowcharts illustrating interrupt routines needed in order to perform the specific frequency superimposing operation. The routine illustrated in FIGS. 9 and 10 is executed in a predetermined cycle, for example, every 1 msec.

In step 901 of the impedance calculating routine illustrated in FIG. 9, the ECU 100 determines whether an ignition switch IGSW (not shown) is on or off. If the ignition switch IGSW is on, the operation proceeds to step 902. If the ignition switch IGSW is off, the present cycle of the routine ends. In step 902, the ECU 100 determines whether a DC voltage Vm (=0.3 V) is already applied to the air-fuel ratio sensor 101. If the determination is affirmative, the operation proceeds to step 903. If the determination in step 902 is negative, the operation proceeds to step 904. In step 904, the ECU 100 applies the DC voltage of 0.3 V to the air-fuel ratio sensor 101.

In step 903, the ECU 100 determines whether 4 msec has elapsed (it is substantially exactly 4 ms) following the application of the DC voltage of 0.3 V to the air-fuel ratio sensor 101 in step 904 and/or whether 4 ms has elapsed (it is substantially exactly 4 ms) following the reading of the current Ims of the air-fuel ratio sensor 101 in the previous cycle of the routine, on the basis of, for example, a counter. If either one of the determination results is affirmative, the operation proceeds to step 905. If both determination results are negative, the present cycle of the routine ends. In step 905, the ECU 100 reads the current Ims of the air-fuel ratio sensor 101, and goes to step 1001 in FIG. 10.

The specific frequency superimposing operation in the sensor element impedance calculating routine will be described with reference to the flowcharts of FIGS. 10 through 12. The following description will be made, assuming that the specific frequency is 5 kHz. In step 1001, the ECU 100 determines whether the present cycle is at the elapse of k×64 msec (k=1, 2, 3, . . . ) following the start of the routine, for example, using a counter. If the determination is affirmative, that is, if the present operation cycle is at the elapse of one of 64 msec, 128 msec, 192 msec, . . . , the operation proceeds to step 1002. If the determination in step 1001 is negative, the present cycle of the routine ends. In step 1002, the ECU 100 superimposes a pulse voltage of −0.2 V on the applied voltage Vm (=0.3 V) for the air-fuel ratio sensor 101, so that the voltage presently applied to the air-fuel ratio sensor 101 becomes 0.1 V. In step 1002, a first timer interrupt illustrated in FIG. 11 is started.

The first timer interrupt operation will be described with reference to the flowchart of FIG. 11. In step 1101, the ECU 100 determines whether 85 $\mu$s has elapsed following the start of the first timer interrupt. If the determination is affirmative, the operation proceeds to step 1102, in which the ECU 100 reads the output current Im1 of the air-fuel ratio sensor 101. If the determination in step 1101 is negative, the operation returns to step 1101 (step 1101 is repeated).

In step 1103, the ECU 100 determines whether 100 82 s has elapsed following the start of the first timer interrupt. If the determination is affirmative, the operation proceeds to step 1104, in which the ECU 100 applies a voltage of Vm (=0.5V) to the air-fuel ratio sensor 101. If the determination in step 1103 is negative, the operation returns to step 1101. In step 1104, a second timer interrupt illustrated in FIG. 12 is started.

The second timer interrupt operation will be described with reference to FIG. 12. In step 1201, the ECU 100 determines whether 100 $\mu$s has elapsed following the start of the second timer interrupt. If the determination is affirmative, the operation proceeds to step 1202, in which the ECU 100 applies a voltage of Vm (=0.3 V) to the air-fuel ratio sensor 101, thereby resetting the sensor to a normal state for air-fuel detection. If the determination in step 1201 is negative, the operation returns to step 1201 (step 1201 is repeated).

Referring back to FIG. 10, in step 1003, the ECU 100 determines whether the present operation cycle is at the elapse of (k×64+4) msec (k=1, 2, 3, . . . ) following the start of this routine. If the determination is affirmative, the operation proceeds to step 1004. If the determination in step 1003 is negative, the present cycle of the routine ends.

In step 1004, the ECU 100 calculates an impedance Zac at the time of application of a specific frequency voltage, from equation (1):

$$Zac=\Delta Vm/\Delta Im=0.2/(Im-Ims) \qquad (1)$$

In step 1005, the ECU 100 performs a Zac guard operation such that the impedance Zac will be within the range between a lower limit guard value KREL and an upper limit guard value KREH, that is, KREL$\leq$Zac$\leq$KREH. More specifically, if the present impedance Zac is within the range KREL$\leq$Zac$\leq$KREH, the present impedance Zac is maintained. If Zac<KREL, then the impedance Zac is changed to the lower limit KREL, that is, Zac=KREL=1 ($\Omega$). If KREH<Zac, then Zac is changed to the upper limit KREH, that is, Zac=KREH=200 ($\Omega$). The guard operation is normally performed in order to ignore data produced by external disturbance, A/D conversion error, or the like.

Figure 13:
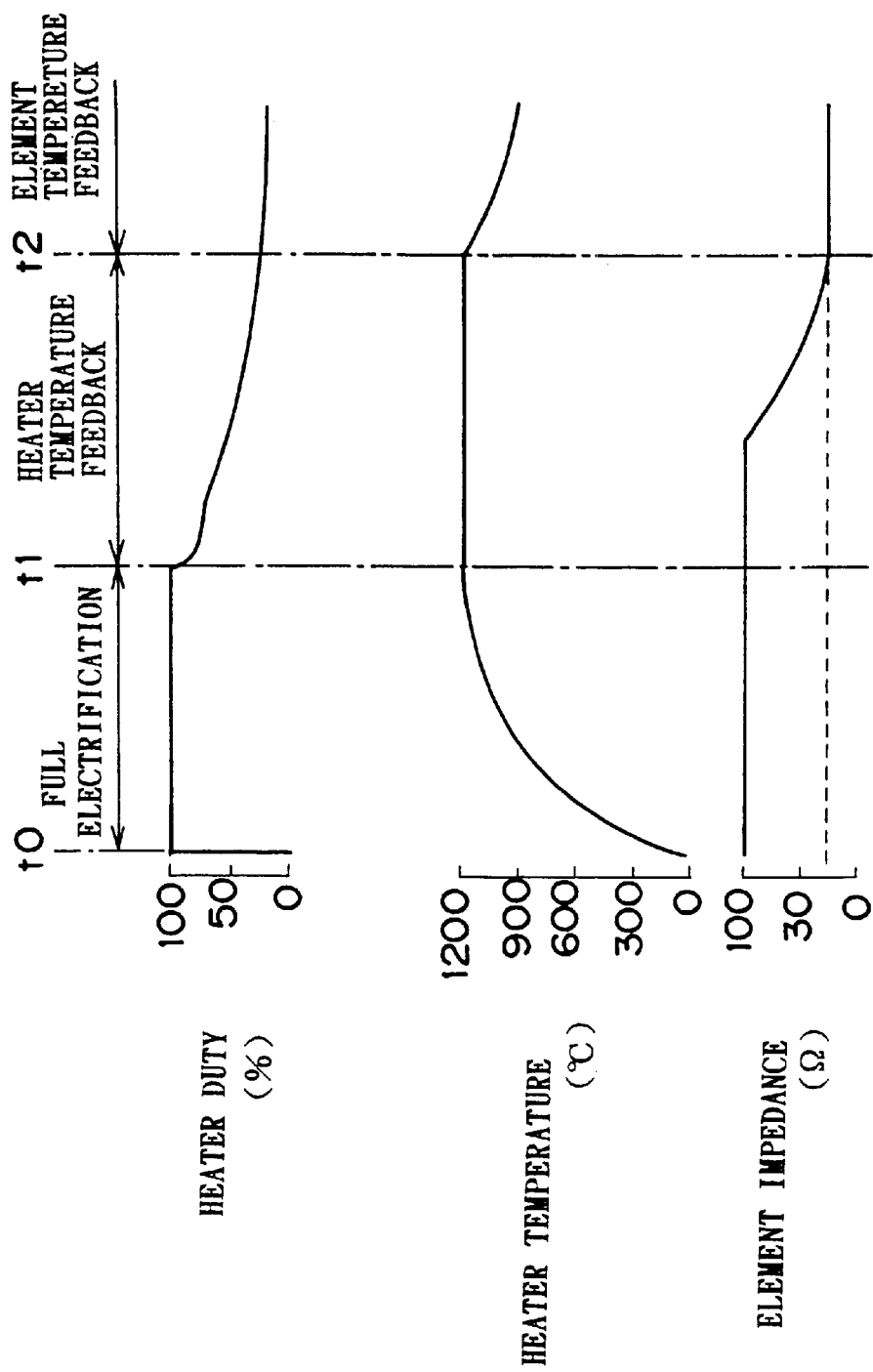
FIG. 13 is a time chart of a heater control operation.

FIG. 13 is a time chart of a heater control operation. In FIG. 13, the horizontal axis indicates time, and the vertical axis indicates the duty ratio of power supplied to the heater 104 in an upper portion of the chart, and the heater temperature in an intermediate portion of the chart, and the element impedance in a lower portion of the chart. When the engine 1 is started, a full electrification control with a duty ratio of 100% is performed during a period between time t0 at which heater electrification is started and time t1 at which the heater temperature reaches a target (upper limit) temperature, for example, 1200° C. During a period between time t1 to time 2 at which the sensor element impedance reaches 30$\Omega$ corresponding to an element temperature of 700° C., at which the sensor element is activated, a heater temperature feedback control is performed to keep the heater 104 at the target temperature. After time t2, an element temperature feedback control is performed to keep the sensor element temperature at the element activation temperature of 700° C. This heater control routine will be described below with reference to flowcharts.

Figure 14:
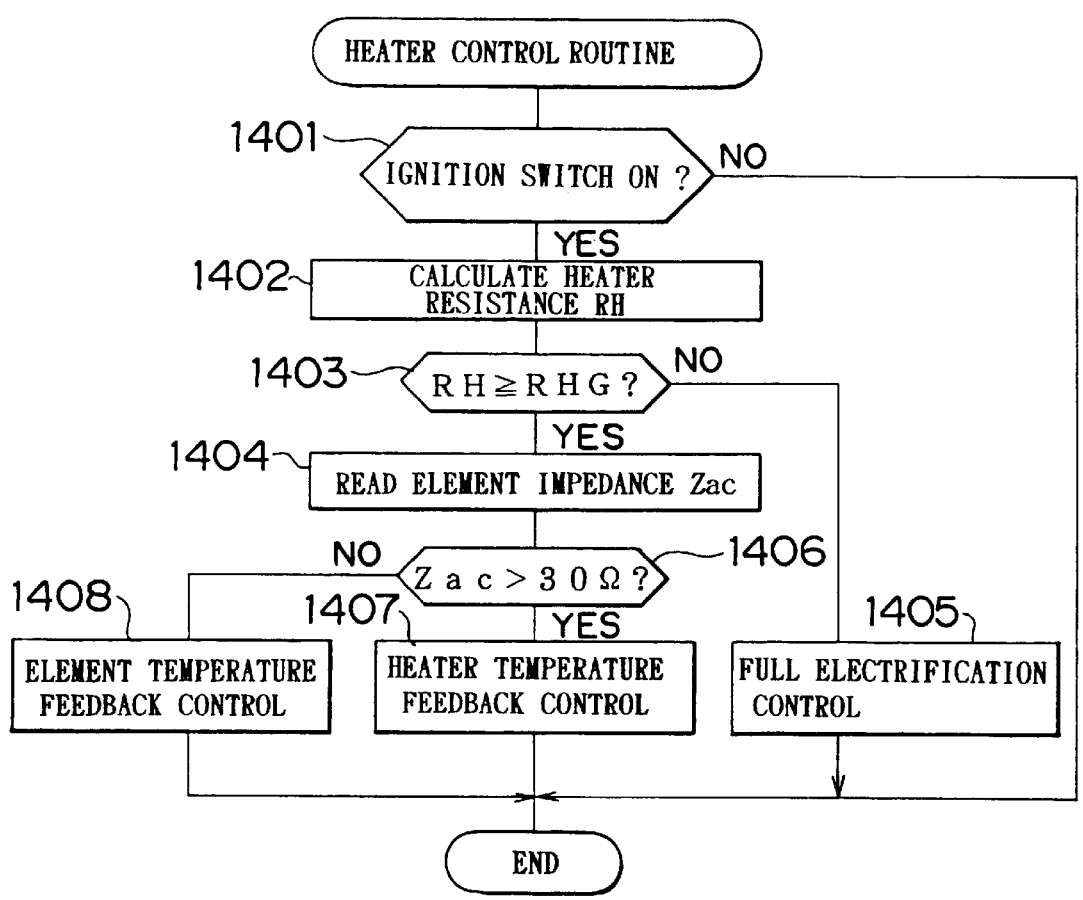
FIG. 14 is a flowchart illustrating a heater control routine.

FIG. 14 is a flowchart illustrating the heater control routine. This routine is executed in a predetermined cycle, for example, every 100 msec. In step 1401, the ECU 100 determines whether the ignition switch (not shown) is on or off. If the ignition switch is on, the operation proceeds to step 1402. If the ignition switch is off, the present cycle of the routine ends. In step 1402, the ECU 100 calculates a heater resistance RH from the voltage applied to the heater 104 and the current flowing through the heater 104. Subsequently in step 1403, the ECU 100 compares the heater resistance RH calculated in step 1402 with a heater resistance learned value RHG. If RH$\geq$RHF (YES in step 1403), then the operation proceeds to step 1404. If RH<RHG, then the operation proceeds to step 1405. The "heater resistance learned value RHG" is a value learned from heater resistance values occurring whe the heater temperature equals the target temperature (1200° C.) so that the learned value eliminates the problem of variations in resistance due to individual product differences, aging changes, or the like.

In step 1404, the ECU 100 reads an element impedance Zac. Subsequently in step 1406, the ECU 100 compares the impedance Zac read in step 1404 with 30Ω, that is, the resistance value corresponding to the sensor element activation temperature. If Zac>30, it is considered that the sensor element 102 is in the active state, and the operation proceeds to step 1408. If Zac≦30 (NO in step 1406), it is considered that the sensor element 102 is in the inactive state, and the operation proceeds to step 1407. In step 1405, the ECU 100 performs the full electrification (100% duty) control. In step 1407, the ECU 100 performs the heater temperature feedback control. In step 1408, the ECU 100 performs the element temperature feedback control. The element temperature feedback control routine for maintaining the temperature of the air-fuel ratio sensor element 102 at the activation temperature on the basis of the impedance Zac of the air-fuel ratio sensor 101 detected by applying the specific frequency to the sensor will be described below.

Figure 15:
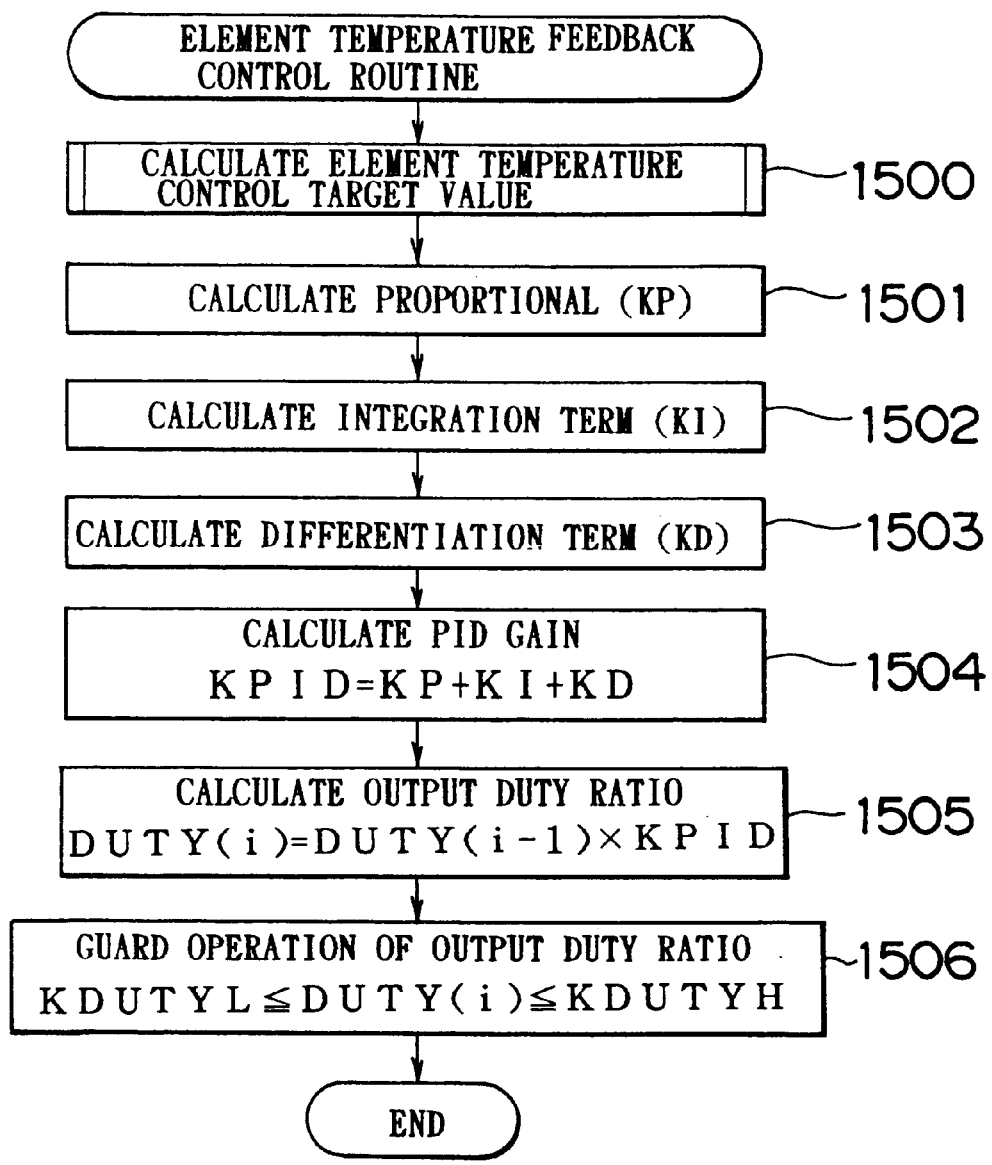
FIG. 15 is a flowchart illustrating a sensor element temperature feedback control routine.

FIG. 15 is a flowchart illustrating the element temperature feedback control routine. This routine is performed in a predetermined cycle, for example, every 128 msec. In this routine, the PID control of heater electrification duty ratio is performed on the basis of the deviation Zacerr of the impedance Zac of the air-fuel ratio sensor 101 corresponding to the specific frequency of 5 kHz from a target impedance Zactg (Zecerr=Zactg−Zac). In step 1500, the ECU 100 executes a target impedance calculating routine described later.

Subsequently in step 1501, the ECU 100 calculates a proportional KP as in equation (2):

$$KP = Zacerr \times K1 \ (K1\text{: constant}) \quad (2)$$

Subsequently in step 1502, the ECU 100 calculates an integration term KD as in equation (3):

$$KI = \Sigma zacerr \times K2 \ (K2\text{: constant}) \quad (3)$$

In step 1503, the ECU 100 calculates a differentiation term KD as in equation (4):

$$KD = (\Delta zacerr / \Delta t) \times K3 \ (K3\text{: constant}) \quad (4)$$

In step 1504, the ECU 100 calculates a PIC gain KPID as in equation (5):

$$KPID = KP + KI + KD \quad (5)$$

In step 1505, the ECU 100 calculates an output duty ratio as in equation (6):

$$DUTY(i) = DUTY(i-1) \times KPID \quad (6)$$

In step 1506, the ECU 100 performs a guard operation for the output duty ratio DUTY(i) such that the duty ratio DUTY(i) will be within the range between a lower limit value KDUTYL and an upper limit value KDUTYH, that is, HDUTYL≦DUTY(i)≦KDUTYH. More specifically, if the duty ratio DUTY(i) is within the range, that is, KDUTYL≦DUTY(i)≦KDUTYH, then the duty ratio DUTY(i) is maintained. If DUTY(i)≦KDUTYL, then the duty ratio DUTY(i) is changed to the lower limit, that is, DUTY(i)=KDUTYL. If KDUTYH<DUTY(i), then DUTY(i) is changed to the upper limit, that is, DUTY(i)=KDUTYH.

In the heater control illustrated in FIGS. 13 and 14, the resistance detecting apparatus according to the invention performs an operation as described below, in order to prevent over-temperatures of the heater 104 and the sensor element 102. That is, the resistance detecting apparatus determines whether the air-fuel ratio sensor impedance Zac in response to the specific frequency of 5 kHz is equal to or less than a value obtained by subtracting a predetermined value, for example, 5Ω, from a target impedance Zactg provided after the deterioration correction (Zac≦Zactg−5 (Ω)). If the determination is affirmative, it is considered that the heater temperature and the sensor element temperature are normal, that is, the heater 104 and the sensor element 102 do not have over-temperatures. Then, the heater control routine illustrated in FIG. 14 is performed. If the determination is negative, it is considered that the heater temperature or the element temperature is abnormal, that is, the heater and the sensor element have over-temperatures. Then, the operation of setting DUTY(i)=0 is performed.

Next described will be a routine of calculating a target impedance Zactg on the basis of an element temperature control target learned value Zactgg obtained by estimating and learning the aging change of the sensor element 102, and in accordance with gas conditions of the detection object gas detected by the sensor element 102.

FIG. 16 is a flowchart illustrating a target impedance calculating routine. This routine is executed in a predetermined cycle, for example, every 100 msec. In step 1601, the ECU 100 learns the deterioration of the sensor element 102, and correspondingly calculates an element temperature control target learned value Zactgg, and stores the learned value into the backup RAM 44. The element temperature control target learned value Zactgg can be calculated by, for example, calculating a mean amount of electric power supplied to the heater 104 of the sensor element 102 as described below. This learned value is read into the backup RAM 44 by the initial setting performed at start of the engine.

Subsequently in step 1602, the ECU 100 calculates an impedance correction amount KLD from an intake air flow ga (g/sec) read from the air flow meter 9, on the basis of a map (shown in FIG. 17) for deriving an impedance correction amount KLD from the intake air flow ga. As can be seen from the map shown in FIG. 17, the correction amount KLD is set to zero for a predetermined value (20 g/sec) of the intake air flow, and the correction amount KLD is set to decreasing (negative) correction values for intake air flows lower than the predetermined value, and set to increasing (positive) correction values for the higher intake air flows. The map is thus set since as the intake air flow increases, the sensor element electrode interface resistance increases and therefore the element impedance increases.

In step 1602, the impedance correction amount KLD may also be calculated on the basis of a map (shown in FIG. 18) for deriving an impedance correction amount KLD from the engine load condition. As can be understood from the map shown in FIG. 18, an engine load condition is estimated from the engine revolution speed NE (rpm) calculated based on detection signals from crank angle sensors 33, 34 and an intake pipe negative pressure (mmHg) detected by an intake air pressure sensor. The correction amount KLD is set to zero in intermediate load conditions, and assumes decreasing (negative) correction values in low-load low-speed conditions, and assumes increasing (positive) correction values in high-load high-speed conditions. The map is thus set since as the condition shifts toward a higher-load higher-speed side, the intake air flow increases, so that the sensor element electrode interface resistance increases and therefore the element impedance increases.

As for the engine load, a value ga/NE calculated from a revolution speed NE (rpm) and an intake air flow ga (g/sec) detected by the air flow meter 9 may also be used as a substitute.

Subsequently in step 1603, the ECU 100 calculates an impedance correction amount KAF from an air-fuel ratio (A/F) read from the air-fuel ratio sensor 101, on the basis of a map (shown in FIG. 19) for deriving a correction amount KAF from the air-fuel ratio (A/F) of the engine 1. As shown in the map in FIG. 19, the correction amount KAF is set to zero for the theoretical air-fuel ratio (A/F) 14.5, and it is set to increasing (positive) correction values for air-fuel ratios lower than the theoretical air-fuel ratio, and decreasing (negative) correction values for the higher air-fuel ratios. The map is thus set since as the air-fuel ratio increases, the amount of oxygen decreases, so that the sensor element electrode interface resistance decreases and therefore the element impedance decreases.

Subsequently in step 1604, the ECU 100 calculates a target impedance Zactg from the element temperature control target learned value Zactgg, the correction amount KLD based on the intake air flow or the load, and the correction amount KAF based on the air-fuel ratio, which were calculated in steps 1601–1603, as in equation (7):

$$Zactg = Zactgg + KLD + KAF \qquad (7)$$

By varying the target impedance in the manner described above, overheating of the heater resistor and the sensor element 102 can be prevented.

Next described will be a routine of calculating a cumulative amount of electric power supplied to the heater 104 during a predetermined period, and determining a degree of deterioration of the air-fuel ratio sensor 101 based on the calculated cumulative amount of electric power, and calculating an element temperature control target learned value Zactgg of the impedance of the air-fuel ratio sensor 101.

Figure 20:
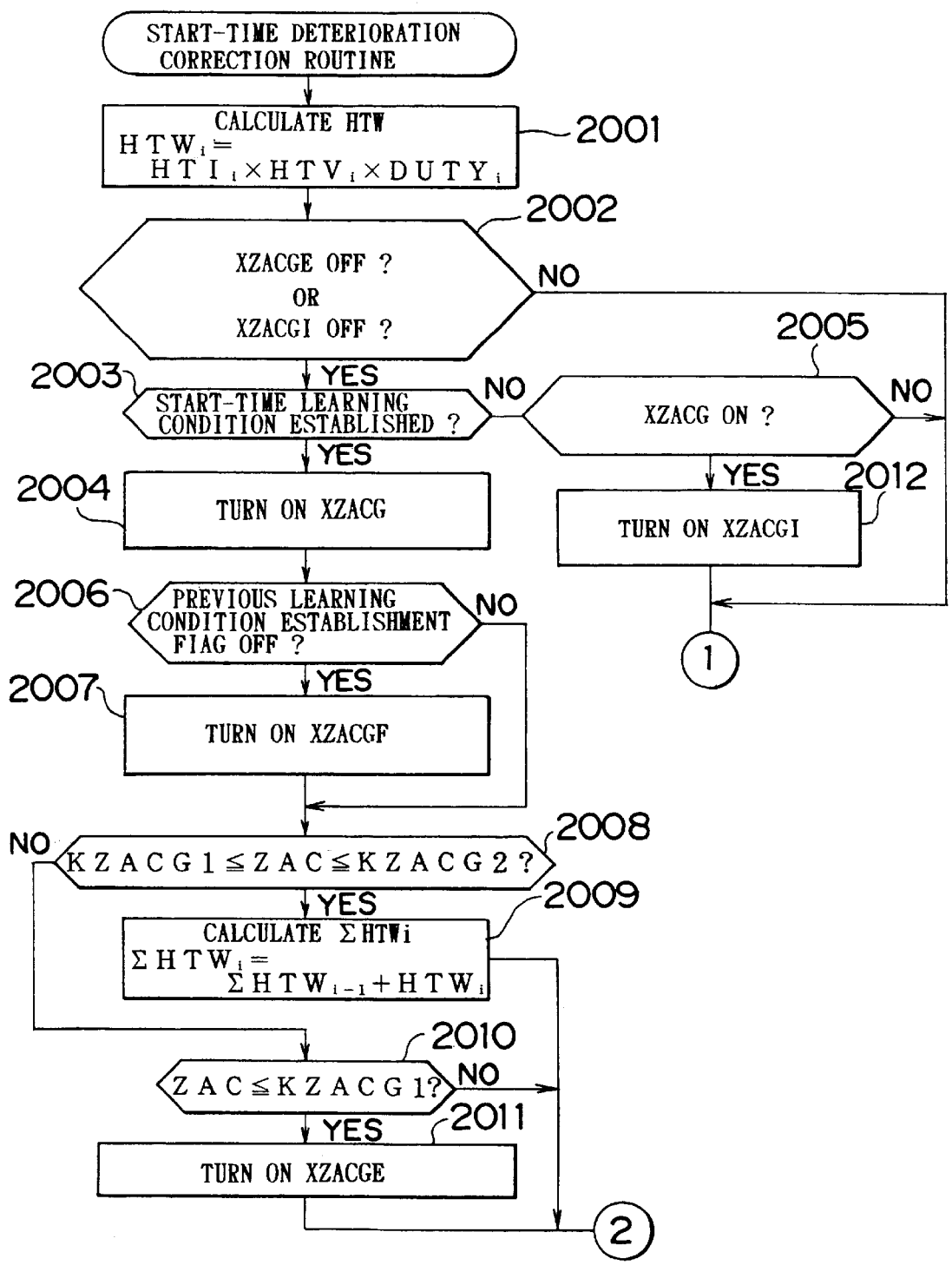
FIG. 20 is a flowchart illustrating an earlier portion of an element deterioration correction routine performed at start of the engine.
Figure 21:
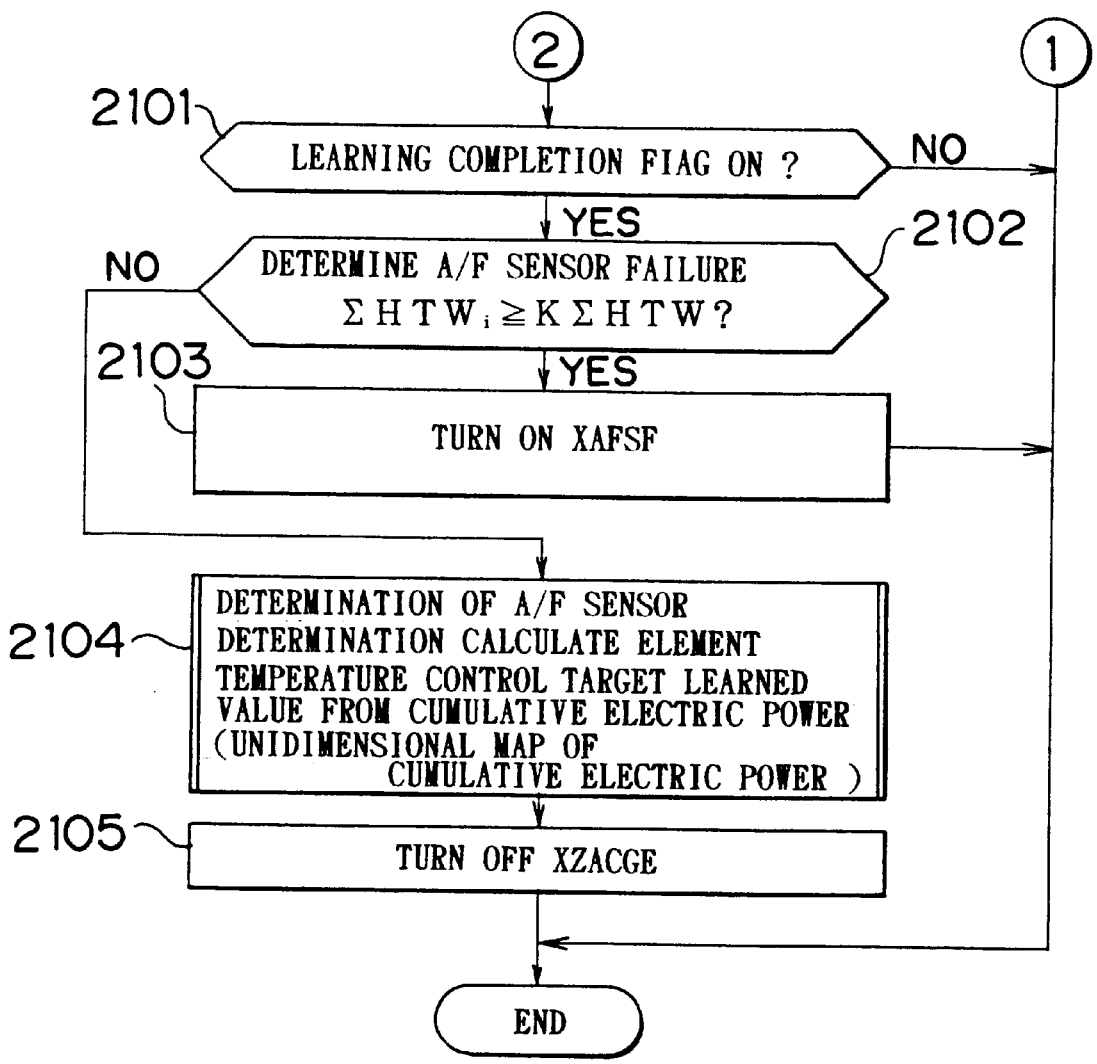
FIG. 21 is a flowchart illustrating the later portion of the element deterioration correction routine.

FIG. 20 is a flowchart illustrating an earlier portion of an element deterioration correction routine performed at start of the engine 1. FIG. 21 is a flowchart illustrating the later portion of the element deterioration correction routine. This routine is executed in a predetermined cycle, for example, every 128 msec. In step 2001, the ECU 100 reads the present current HTIi through the heater resistor, the voltage HTVi applied to the heater resistor, and the duty ratio DUTYi of the heater power supply, and calculates a power HTWi supplied to the heater resistor (HTWi=HTIi×HTVi×DUTYi). Subsequently in step 2002, the ECU 100 checks whether a learning completion flag XZACGE is off or whether a learning inhibition flag XZACGI is off. If the determination is affirmative, the operation proceeds to step 2003. If the determination is negative, the present cycle of the routine ends.

In step 2003, the ECU 100 determines whether a condition for the learning at start of the engine has been established. If the determination is affirmative, the operation proceeds to step 2004. If the determination is negative, the operation proceeds to step 2005.

The engine start-time learning condition is considered to have been established if the conditions listed below are met, the conditions indicating that the engine 1 is in a cold steady idle state.

The water temperature THWst after start of the engine is within a predetermined range (THW1≦THWst≦THW2).
The battery voltage BATst after start of the engine is equal to or greater than a predetermined value (KBA≦BATst).
The impedance Zacst (Ω) of the air-fuel ratio sensor after start of the engine is equal to or greater than a predetermined value (KZac≦Zacst).
The engine revolution speed NE (rpm) is equal to or lower than a predetermined value (NE≦KNE).
The engine intake pressure PM (mmHG) is equal to or lower than a predetermined value (PM≦KPM).
The vehicle speed SPD (km/h) is equal to or lower than a predetermined value (SPD≦KSPD).
The engine idle switch is on.

In step 2004 following the affirmative determination in step 2003, the ECU 100 turns on a learning condition establishment flag XZACG. On the other hand, in step 2005 following the negative determination in step 2003, the ECU 100 checks whether a first learning condition establishment flag XZACGF that indicates the first establishment of the learning condition after start of the engine is on. If the flag is on (XZACGF=1), the operation proceeds to step 2012. If the flag is off (ZXACGF=0) the present cycle of the routine ends.

In step 2006 following step 2004, the ECU 100 checks whether the learning condition establishment flag XZACG was on in the previous operation cycle. If the flag was off (ZXACG=0) in the previous cycle, the operation proceeds to step 2007. If the flag was on (XZACG=1), the operation proceeds to step 2008. In step 2007, the ECU 100 turns on the first learning condition establishment flag XZACGF.

In step 2008, the ECU 100 determines whether the element impedance Zac of the air-fuel ratio sensor 101 is within a predetermined range (KZacG1≦Zac≦KZacG2 where KZacG1 is a lower limit value, that is, an element impedance corresponding to an element temperature of 600° C., and KZacG2 is an upper limit value, that is, an element impedance corresponding to an element temperature of 400° C.). If the determination in step 2008 is affirmative, the operation proceeds to step 2009. If the determination is negative, the operation proceeds to step 2010. In step 2009, the ECU 100 calculates a cumulative amount of electric power ΣHTWi up to the present operation cycle as in equation (8):

$$\Sigma HTWi = \Sigma HTWi-1 + HTWi \qquad (8)$$

In equation (8), ΣHTWi–1 represents a cumulative amount of electric power up to the previous operation cycle. The value ΣHTWi–1 is cleared to zero immediately after the engine is started by turning on the ignition switch. After step 2009, the operation proceeds to step 2101 in FIG. 21.

In step 2010 following the negative determination in step 2008, the ECU 100 determines whether the impedance Zac of the air-fuel ratio sensor 101 is equal to or less than the predetermined value KZacGl (Zac≦KZacG1). If the determination is affirmative, the operation proceeds to step 2011. If the determination is negative, the operation proceeds to step 2101 in FIG. 21. in step 2011, the ECU 100 turns on the learning completion flag XZACGE.

In step 2101, the ECU 100 checks whether the learning completion flag XZACGE is on. If the learning completion flag is on (XZACGE=1), the operation proceeds to step 2102. If the learning completion flag is off (XZACGE=0), the present operation cycle of the routine ends. In step 2102, the ECU 100 determines whether the air-fuel ratio sensor 101 has a failure. That is, the ECU 100 determines whether the cumulative amount of electric power ΣHTWi calculated in the present operation cycle is equal to or greater than a predetermined value KΣHTW (ΣHTWi≧KΣHTW). If the determination is affirmative, the ECU 100 determines that the air-fuel ratio sensor 101 has a failure, and goes to step 2103. If the determination is negative, the ECU 100 goes to step 2104. In step 2103, the ECU 100 turns on an air-fuel ratio sensor failure flag XAFSF. Subsequently, the present cycle of the routine ends.

In step 2104, the ECU 100 executes a routine of calculating an element temperature control target learned value Zactgg from a heater cumulative amount of electric power $\Sigma HTWi$ as described below with reference to the flowchart in FIG. 25. Subsequently in step 2105, the ECU 100 turns off the learning completion flag XZACGE. A routine of correcting for element deterioration during engine idle will be described below.

Figure 22:
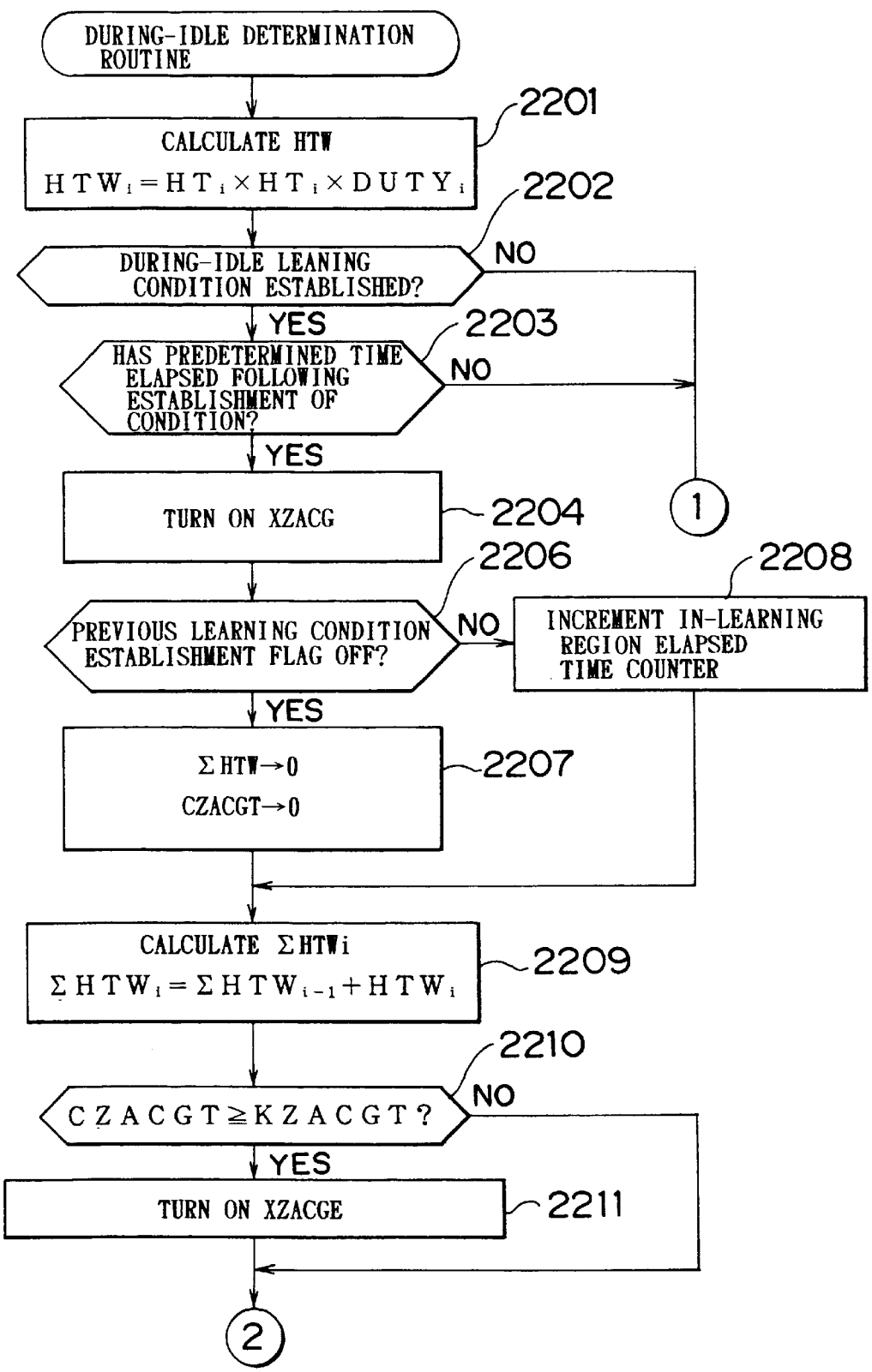
FIG. 22 is a flowchart illustrating an earlier portion of a during-idle element deterioration correction routine.

FIG. 22 is a flowchart illustrating an earlier portion of the during-idle element deterioration correction routine. This routine is executed in a predetermined cycle, for example, every 128 msec. In step 2201, the ECU 100 reads the present current HTIi through the heater resistor, the voltage HTVi applied to the heater resistor, and the duty ratio DUTYi of the heater power supply, and calculates a power HTWi supplied to the heater resistor ($HTWi = HTIi \times HTVi \times DUTYi$).

Subsequently in step 2202, the ECU 100 determines whether a condition for the learning during engine idle has been established. If the determination is affirmative, the operation proceeds to step 2203. If the determination is negative, the present cycle of the routine ends.

The during-idle leaning condition is considered to have been established if the conditions listed below are met, the condition indicating that the engine 1 is in a complete warm-up steady idle state.

The water temperature THWst after start of the engine is within a predetermined range ($THW1 \leq THWst \leq THW2$).
The battery voltage BAT is equal to or greater than a predetermined value ($KBA \leq BAT$).
The impedance Zac ($\Omega$) of the air-fuel ratio sensor is within a predetermined range ($KZac1 \leq Zac \leq KZac2$).
The engine revolution speed NE (rpm) is equal to or lower than a predetermined value ($NE \leq KNE$).
The engine intake pressure PM (mmHG) is equal to or lower than a predetermined value ($PM \leq KPM$).
The vehicle speed SPD (km/h) is equal to or lower than a predetermined value ($SPD \leq KSPD$).
The engine idle switch is on.

Subsequently in step 2203 following the affirmative determination in step 2202, the ECU 100 determines whether a predetermined length of time has elapsed following establishment of the learning condition. If the determination is affirmative, the operation proceeds to step 2204. If the determination is negative, the present cycle of the routine ends. In step 2204, the ECU 100 turns on the learning condition establishment flag XZACG.

Subsequently in step 2206, the ECU 100 checks whether the learning condition establishment flag XZACG was off in the previous operation cycle. If the flag was off (XZACG=0), the operation proceeds to step 2207. If the flag was on (XZACG=1), the operation proceeds to step 2208. In step 2207, the ECU 100 clears the cumulative amount of electric power $\Sigma HTWi$ to zero, and clears an in-learning region elapsed time counter CZACGT to "0".

In step 2208 following the negative determination in step 2206, the ECU 100 increments the in-learning region elapsed time counter CZACGT (CZACGT=CZACGT+1).

In step 2209, the ECU 100 calculates a cumulative amount of electric power $\Sigma HTWi$ up to the present operation cycle as in equation (9):

$$\Sigma HTWi = \Sigma HTWi-1 + HTWi \quad (9)$$

In equation (9), $\Sigma HTWi-1$ represents a cumulative amount of electric power up to the previous operation cycle.

The value $\Sigma HTWi-1$ is cleared to zero immediately after the engine is started by turning on the ignition switch.

Subsequently in step 2210, the ECU 100 determines whether the value of the in-learning region elapsed time counter CZACGT is equal to or greater than a predetermined value KCZACGT ($CZACGT \geq KCZACGT$). If the determination is affirmative, the operation proceeds to step 2211. If the determination is negative, the operation proceeds to step 2101 in FIG. 21. In step 2211, the ECU 100 turns on the learning completion flag XZACGE. A routine of correcting for element deterioration during vehicle travel will be described below.

Figure 23:
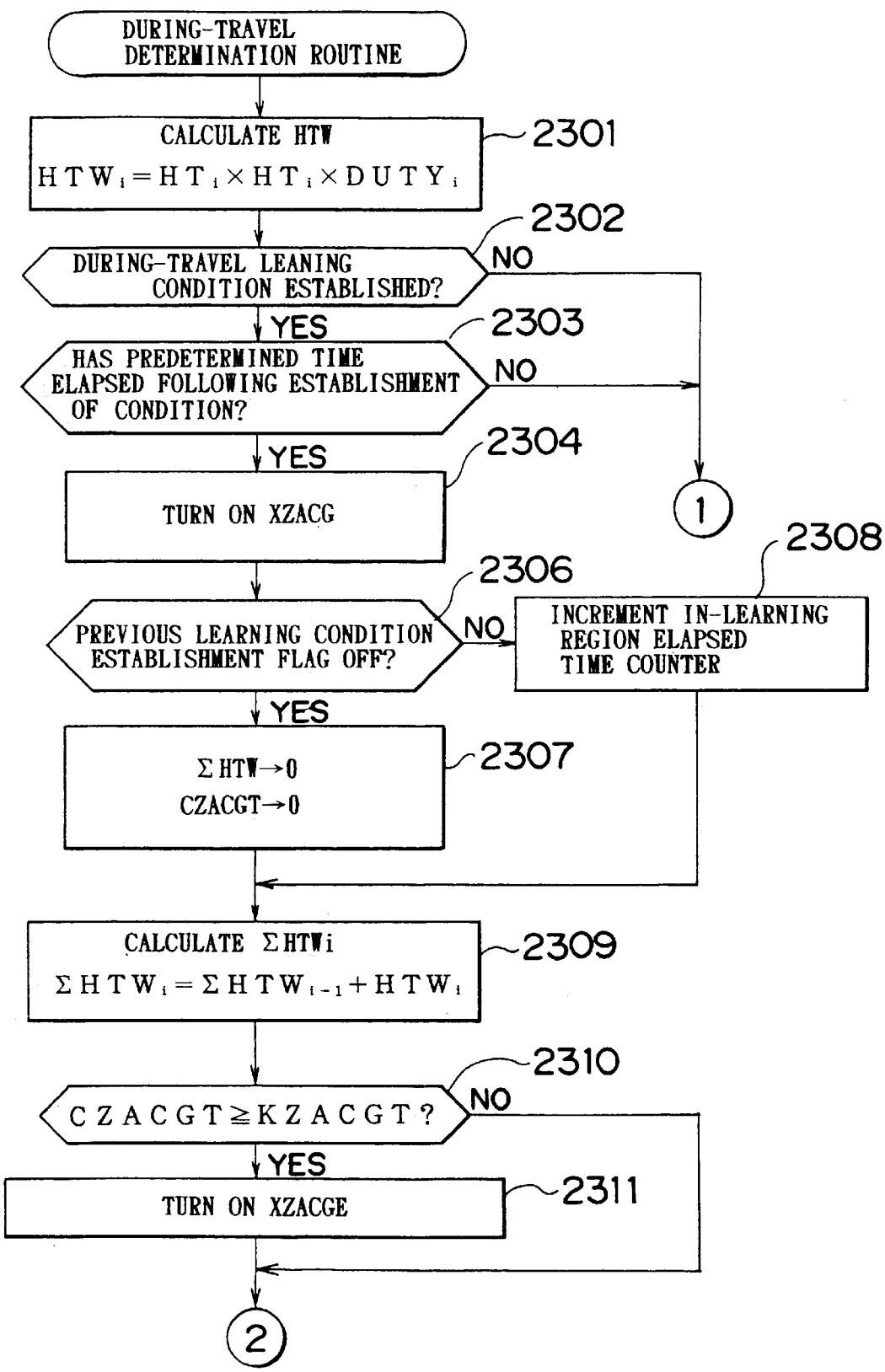
FIG. 23 is a flowchart illustrating an earlier portion of a during-travel element deterioration correction routine.

FIG. 23 is a flowchart illustrating an earlier portion of the during-travel element deterioration correction routine.

The during-travel element deterioration correction routine illustrated in FIG. 23 is substantially the same as the during-idle element deterioration correction routine illustrated in FIG. 22, except that in step 2302 in FIG. 23 it is determined whether a during-travel learning condition has been established whereas in step 2202 in FIG. 22 it is determined whether the during-idle learning condition has been established. The condition for the learning during travel in step 2302 will be described below, while the other steps will not be described again.

The during-travel learning condition is considered to have been established if the conditions listed below are met, the conditions indicating that the engine is in a complete warm-up steady running state.

The water temperature THWst after start of the engine is within a predetermined range ($THW1 \leq THWst \leq THW2$).
The battery voltage BAT is equal to or greater than a predetermined value ($KBA \leq BAT$).
The impedance Zac ($\Omega$) of the air-fuel ratio sensor is within a predetermined range ($KZac1 \leq Zac \leq KZac2$).
The engine revolution speed NE (rpm) is within a predetermined range ($KNE1L \leq NE \leq KNE1H$).
The engine load factor smoothing value KLSM (%) is within a predetermined range $KKLSM1L \leq KLSM \leq KKLSM1H$).

Although the three modes of the element deterioration correction routine performed at start of the engine, during idle, and during travel have been described, it is not necessary to perform all the three modes, that is, it is possible to perform element deterioration correction based on any one or any combination of the three modes, according to the invention.

An operation performed after the air-fuel ratio sensor failure determination will next be described.

Figure 24:
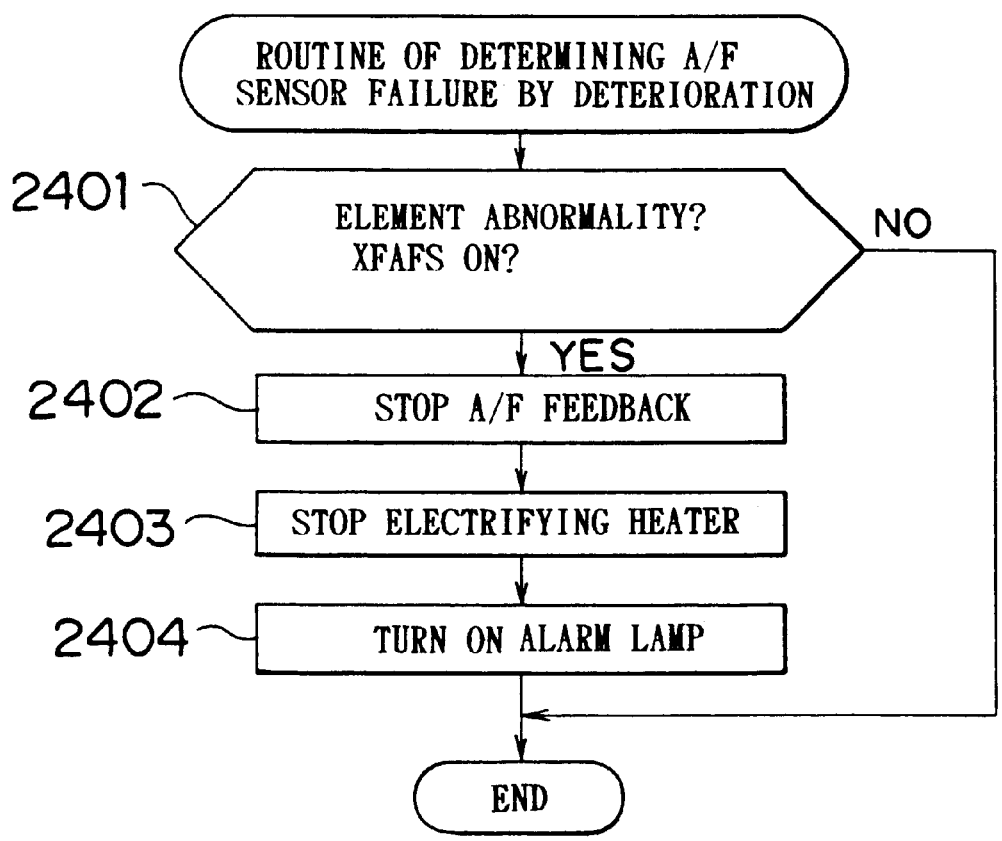
FIG. 24 is a flowchart illustrating an air-fuel ratio sensor failure determining routine.

FIG. 24 is a flowchart illustrating an air-fuel ratio sensor failure determining routine. This routine is executed in a predetermined cycle, for example, every 128 msec. In step 2401, the ECU 100 determines whether an air-fuel ratio sensor failure determination flag XFAFS is on. If the flag is on (XFAFS=1), the operation proceeds to step 2402. If the flag is off (XFAFS=0), the present cycle of the routine ends. In step 2402, the ECU 100 stops an air-fuel ratio feedback control operation for controlling the exhaust air-fuel ratio of the engine 1 to a target air-fuel ratio, for example, the theoretical air-fuel ratio. Subsequently in step 2403, the ECU 100 stops electrifying the heater 104 to prevent overheating of the heater 104. Subsequently in step 2404, the ECU 100 turns on an alarm lamp (not shown) to inform a driving person of the occurrence of an air-fuel ratio sensor failure. Below described will be the operation in step 2104 in FIG. 21, that is, a routine of correcting the target impedance Zactg on the basis of the heater cumulative amount of electric power $\Sigma HTWi$.

Figures 25, 26:
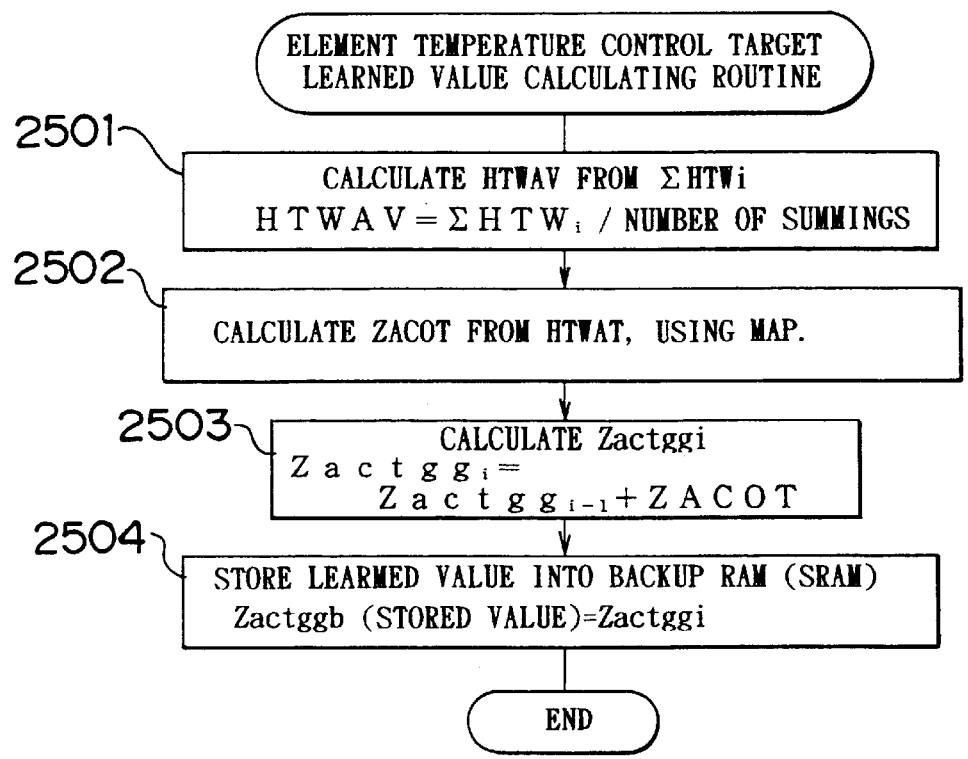
FIG. 25 is a flowchart illustrating an element temperature control target learned value calculating routine.
FIG. 26 illustrates a map for deriving a correction amount for the element temperature control target learned value, from a mean amount of electric power supplied to the heater.

FIG. 25 is a flowchart illustrating an element temperature control target learned value calculating routine. This routine is executed in a predetermined cycle, for example, every 128 msec. In step 2501, the ECU 100 calculates a mean electric power HTWV from the heater cumulative amount of electric power ΣHTWi as in equation (10):

$$HTWAV = \Sigma THWi/\text{number of summings} \qquad (10)$$

In step 2502, the ECU 100 calculates a correction amount ZACOT (Ω) for the element temperature control target learned value Zactgg for estimation of the deterioration of the sensor element 102, from the mean electric power HTWAV (W·h) on the basis of a map indicated in FIG. 26. Subsequently in step 2503, the ECU 100 calculates an element temperature control target learned value Zactggi for the present operation cycle as in equation (11):

$$Zactggi = Zactggi - 1 + ZACOT \qquad (11)$$

In equation (11), Zactggi−1 is the element temperature control target learned value used in the previous operation cycle. Subsequently in step 2504, the ECU 100 performs an updating operation regarding the presently-obtained element temperature control target learned value Zactggi as in equation (12), and stores it into a battery-backup SRAM.

$$Zactggb = Zactggi \qquad (12)$$

As is apparent from FIG. 26, the map is set so that the correction amount ZACOT increases as the mean electric power HTWAV increases. This setting is adopted for the following reason. As the air-fuel ratio sensor deteriorates, the impedance characteristic of the sensor element changes. In response, the control for increasing the sensor element temperature, that is, the control for decreasing the element temperature control target learned value Zactggi, is performed, so that the electric power supplied to the heater increases. In this invention, overheating of the sensor element and the heater resistor is prevented by calculating a mean electric power supplied to the heater, and performing control such that when the calculated mean electric power increases, the element impedance is increased. By preventing overheating of the sensor element and the heater resistor, early deterioration of the sensor element and the heater resistor can be prevented and the service life thereof can be extended.

Although the foregoing embodiment uses a frequency of 5 kHz as a specific frequency, this does not limit the invention. Any suitable specific frequency can be selected by taking into consideration the material of electrodes, the electrolyte and the like of the air-fuel ratio sensor, the characteristic of the sensor circuit, applied voltage, operating temperature, and the like. If a specific frequency that enables detection of impedance up to the sum of R1 (bulk resistance of electrolyte)+R2 (grain boundary resistance of electrolyte)+R3 (electrode interface resistance) indicated in FIGS. 5 and 6 is selected, it becomes possible to monitor changes in the gas condition of the detection object gas more remarkably or more accurately than a case where a frequency that enables detection of impedance only up to R1+R3 is selected.

The air-fuel ratio sensor resistance detecting apparatus of the foregoing embodiment calculates a cumulative amount of electric power supplied to the heater for heating the sensor element, as a parameter of deterioration involved in aging changes of the sensor element, and determines a mean electric power to the heater based on the calculated heater cumulative amount of electric power, and calculates an element temperature control target learned value from the mean electric power, by using the electric power calculating device. Subsequently, the apparatus of the embodiment calculates a correction amount for the sensor target impedance in accordance with gas conditions of the detection object as detected by the sensor element, more specifically, in accordance with the air flow or the load, and the air-fuel ratio. Based on the thus-calculated element temperature control target learned value and the correction amount, the apparatus corrects the impedance of the sensor element and thereby corrects the sensor target impedance. That is, by correcting the element temperature control target learned value based on the cumulative amount of electric power supplied to the heater, which indicates the degree of deterioration of the sensor element caused by aging changes, in accordance with the gas conditions of the detection object gas detected by the sensor element, the apparatus calculates a target impedance. Then, the apparatus performs control such that the sensor element temperature becomes the calculated target impedance. Therefore, the apparatus is able to prevent overheating of the sensor element and the heater.

As is apparent from the above description, the air-fuel ratio sensor resistance detecting apparatus of the invention corrects the impedance of the oxygen concentration detecting element and therefore corrects the element target impedance, in accordance with gas conditions of the detection object gas detected by the oxygen concentration detecting element. Therefore, the apparatus is able to properly control the target impedance in accordance with the gas conditions, so as to prevent overheating of the oxygen concentration detecting element and the heater.

Furthermore, the air-fuel ratio sensor resistance detecting apparatus of the invention corrects the impedance of the oxygen concentration detecting element and therefore corrects the target impedance, in accordance with the amount of electric power supplied to the heater. Therefore, the apparatus is able to properly control the target impedance in accordance with the amount of electric power to the heater, so as to prevent overheating of the oxygen concentration detecting element and the heater.

Still further, the apparatus of the invention is able to determine whether the oxygen concentration detecting element has a failure on the basis of the amount of electric power supplied to the heater within a predetermined length of time.

The apparatus of the invention is also able to detect the impedance of the oxygen concentration detecting element within a short period of time, by applying a voltage obtained by superimposing an AC voltage on a DC voltage to the oxygen concentration detecting element.

While the present invention has been described with reference to what is presently considered to be a preferred embodiment thereof, it is to be understood that the invention is not limited to the disclosed embodiment or constructions. To the contrary, the invention is intended to cover various modifications and equivalent arrangements.

What is claimed is:

1. An apparatus for detecting a resistance of an air-fuel ratio sensor comprising:
   an oxygen concentration detecting element, a current flowing through the oxygen concentration detecting element being proportional to an oxygen concentration of a detection object gas flowing over the oxygen concentration detecting element;
   a heater for activating the oxygen concentration detecting element;
   an air-fuel ratio detector that detects the current flowing through the oxygen concentration detecting element by applying a first voltage to the oxygen concentration detecting element, the air-fuel ratio detector detecting an air-fuel ratio of the detection object gas based on the detected current;

the first voltage being a DC voltage;

a gas condition detector that detects a condition of the detection object gas;

an impedance detector that detects an impedance of the oxygen concentration detecting element by applying a second voltage to the oxygen concentration detecting element, wherein the second voltage is obtained by superimposing an AC voltage on the first voltage;

correction means for correcting the impedance detected by the impedance detector, in accordance with the gas condition; and a controller that controls the electrification of the heater based on the impedance corrected by the correction means.

2. An apparatus for detecting a resistance of an air-fuel ratio sensor, comprising:

an oxygen concentration detecting element, a current flowing through the oxygen concentration detecting element being proportional to an oxygen concentration of a detection object gas flowing over the oxygen concentration detecting element;

a heater for activating the oxygen concentration detecting element;

an air-fuel ratio detector that detects the current flowing through the oxygen concentration detecting element by applying a first voltage to the oxygen concentration detecting element, the air-fuel ratio detector detecting an air-fuel ratio of the detection object gas based on the current;

an electric power calculator that calculates an amount of electric power supplied to the heater;

an impedance detector that detects an impedance of the oxygen concentration detecting element by applying a second voltage to the oxygen concentration detecting element; and correction means for correcting the impedance detected by the impedance detection means, in accordance with the amount of electric power supplied to the heater.

3. An apparatus according to claim 2, wherein the second voltage is obtained by superimposing an AC voltage on the first voltage, the first voltage being a DC voltage.

4. An apparatus according to claim 2, further comprising means for determining whether the oxygen concentration detecting element has a failure on the basis of the amount of electric power calculated by the electric power calculation means.

5. An apparatus according to claim 4, wherein the second voltage is obtained by superimposing an AC voltage on the first voltage, the first voltage being a DC voltage.

6. An apparatus according to claim 2, wherein the electric power calculator calculates a cumulative amount of electric power supplied to the heater during a predetermined period of time.

7. An apparatus according to claim 2, wherein the electric power calculator calculates a mean amount of electric power supplied to the heater during a predetermined period of time.

* * * * *

UNITED STATES PATENT AND TRADEMARK OFFICE
CERTIFICATE OF CORRECTION

PATENT NO.     : 6,382,015 B1
DATED          : May 7, 2002
INVENTOR(S)    : Keiichiro Aoki It is certified that error appears in the above-identified patent and that said Letters Patent is hereby corrected as shown below:

Column 9,
Line 58, replace "100 82 s" with -- 100 $\mu$s --.

Signed and Sealed this

Eleventh Day of February, 2003

JAMES E. ROGAN
*Director of the United States Patent and Trademark Office*